US008889173B2

(12) United States Patent
Zanella et al.

(10) Patent No.: US 8,889,173 B2
(45) Date of Patent: *Nov. 18, 2014

(54) ALPHA ADRENERGIC RECEPTOR AGONISTS FOR TREATMENT OF PAIN AND/OR INFLAMMATION

(75) Inventors: John Myers Zanella, Cordova, TN (US); Sara D. Waynick, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/424,271

(22) Filed: Apr. 15, 2009

(65) Prior Publication Data

US 2009/0263463 A1  Oct. 22, 2009

Related U.S. Application Data

(60) Provisional application No. 61/146,479, filed on Jan. 22, 2009, provisional application No. 61/046,201, filed on Apr. 18, 2008.

(51) Int. Cl.
*A61K 9/14* (2006.01)
*A61K 31/4162* (2006.01)
*A61K 9/00* (2006.01)
*A61K 47/34* (2006.01)
*A61K 9/20* (2006.01)

(52) U.S. Cl.
CPC .............. *A61K 9/0024* (2013.01); *A61K 47/34* (2013.01); *A61K 9/204* (2013.01); *A61K 31/4162* (2013.01)
USPC .......................................... 424/426; 424/501

(58) Field of Classification Search
None
See application file for complete search history.

(56) References Cited

U.S. PATENT DOCUMENTS

| | | |
|---|---|---|
| 3,190,802 A | 6/1965 | Zeile et al. |
| 3,020,660 A | 8/1965 | Zeile et al. |
| 4,624,255 A | 11/1986 | Schenck |
| 4,742,054 A | 5/1988 | Naftchi |
| 4,765,974 A | 8/1988 | Tokuda et al. |
| 4,863,457 A | 9/1989 | Lee |
| 5,175,052 A | 12/1992 | Tokuda et al. |
| 5,447,947 A | 9/1995 | Campbell |
| 5,484,607 A | 1/1996 | Horacek |
| 5,522,844 A | 6/1996 | Johnson |
| 5,626,838 A | 5/1997 | Cavanaugh |
| 5,635,204 A | 6/1997 | Gevirtz et al. |
| 5,759,583 A | 6/1998 | Iwamoto |
| 5,801,188 A | 9/1998 | Hassenbusch, III et al. |
| 5,868,789 A | 2/1999 | Huebner |
| 5,869,100 A | 2/1999 | Horacek |
| 5,942,241 A | 8/1999 | Chasin |
| 5,942,503 A | 8/1999 | Jung et al. |
| 5,942,530 A | 8/1999 | Panetta et al. |
| 5,945,416 A | 8/1999 | Shannon et al. |
| 5,980,927 A | 11/1999 | Nelson et al. |
| 6,030,642 A | 2/2000 | Horacek |
| 6,069,129 A | 5/2000 | Sandberg |
| 6,147,102 A | 11/2000 | Borgman |
| 6,179,862 B1 | 1/2001 | Sawhney |
| 6,248,345 B1 | 6/2001 | Goldenheim |
| 6,287,588 B1 | 9/2001 | Shih |
| 6,326,020 B1 | 12/2001 | Kohane |
| 6,331,311 B1 | 12/2001 | Brodbeck |
| 6,417,184 B1 | 7/2002 | Ockert |
| 6,428,804 B1 | 8/2002 | Suzuki |
| 6,461,631 B1 | 10/2002 | Dunn |
| 6,524,607 B1 | 2/2003 | Goldenheim |
| 6,534,048 B1 | 3/2003 | Borgman |
| 6,534,081 B2 | 3/2003 | Goldenheim |
| 6,589,549 B2 | 7/2003 | Shih |
| 6,630,155 B1 | 10/2003 | Chandrashekar |
| 6,632,457 B1 | 10/2003 | Sawhney |
| 6,723,741 B2 | 4/2004 | Jeon |
| 6,756,058 B2 | 6/2004 | Brubaker |
| 6,773,714 B2 | 8/2004 | Dunn |
| 6,921,541 B2 | 7/2005 | Chasin |
| 6,974,462 B2 | 12/2005 | Sater |
| 6,992,110 B2 | 1/2006 | Kranzler et al. |
| 7,144,412 B2 | 12/2006 | Wolf |
| 7,166,570 B2 | 1/2007 | Hunter |
| 7,220,281 B2 | 5/2007 | Lambrecht |
| 7,229,441 B2 | 6/2007 | Trieu |
| 7,235,043 B2 | 6/2007 | Gellman |

(Continued)

FOREIGN PATENT DOCUMENTS

WO  WO03005961 A2  1/2003
WO  WO2004091540 A2  10/2004

(Continued)

OTHER PUBLICATIONS

Campiglia (Pre-Emptive analgesia for postoperative pain control, A review, Clinical Drug Investigation 30 Suppl. 2: 15-26 (2010)).*
International Search Report and Written Opinion for Application No. PCT/US2009/040896 mailed Dec. 11, 2009.
Aantaa, Riku, MD, PhD, Alpha2-Agonists, Sedatives or Analgesics, Department of Anesthesiology and Intensive Care, University of Turku, Finland, Apr. 15, 2009.
QLT, Inc., Atrigel Drug Delivery Platform, Jul. 2006.
www.medscape.com, Pharmacological Approaches, (2003) or later.
Moberg-Wolff, Spasticity, pp. 1-15, Dec. 21, 2007.

(Continued)

*Primary Examiner* — Robert A Wax
*Assistant Examiner* — H. Sarah Park
(74) *Attorney, Agent, or Firm* — Sorell Lenna & Schmidt LLP

(57) ABSTRACT

Effective treatments of pain and/or inflammation are provided. Through the administration of an effective amount of at least one alpha adrenergic agonist at or near a target site, one can reduce, prevent or treat pain and/or inflammation.

14 Claims, 23 Drawing Sheets

(56) References Cited

U.S. PATENT DOCUMENTS

| | | |
|---|---|---|
| 7,287,983 B2 | 10/2007 | Han |
| 7,318,840 B2 | 1/2008 | McKay |
| 7,329,259 B2 | 2/2008 | Cragg |
| 7,345,065 B2 | 3/2008 | Gil et al. |
| 7,361,168 B2 | 4/2008 | Makower |
| 7,367,978 B2 | 5/2008 | Drewry |
| 7,507,398 B2 | 3/2009 | Rabinowitz et al. |
| 7,524,812 B2 | 4/2009 | Ellis et al. |
| 2002/0009454 A1 | 1/2002 | Boone |
| 2002/0058656 A1 | 5/2002 | Ockert |
| 2002/0090398 A1 | 7/2002 | Dunn |
| 2002/0094998 A1 | 7/2002 | Burke et al. |
| 2003/0022926 A1 | 1/2003 | Lavand'Homme |
| 2003/0118692 A1* | 6/2003 | Wang et al. ............. 426/6 |
| 2003/0185873 A1 | 10/2003 | Chasin |
| 2003/0204191 A1 | 10/2003 | Sater |
| 2003/0224033 A1 | 12/2003 | Li |
| 2004/0028726 A1 | 2/2004 | Fischer et al. |
| 2004/0072799 A1 | 4/2004 | Li |
| 2004/0082540 A1 | 4/2004 | Hermida Ochoa |
| 2004/0101582 A1 | 5/2004 | Wolicki |
| 2004/0109893 A1 | 6/2004 | Chen |
| 2004/0208917 A1 | 10/2004 | Fischer et al. |
| 2004/0214793 A1 | 10/2004 | Hermida Ochoa |
| 2004/0265364 A1 | 12/2004 | Ozturk et al. |
| 2005/0058696 A1 | 3/2005 | Donello et al. |
| 2005/0059744 A1 | 3/2005 | Donello |
| 2005/0095277 A1 | 5/2005 | Ozturk et al. |
| 2005/0142163 A1 | 6/2005 | Hunter |
| 2005/0175709 A1 | 8/2005 | Baty |
| 2005/0186261 A1 | 8/2005 | Avelar |
| 2005/0197293 A1 | 9/2005 | Mellis |
| 2006/0074422 A1 | 4/2006 | Story |
| 2006/0106361 A1 | 5/2006 | Muni |
| 2006/0148903 A1 | 7/2006 | Burch |
| 2006/0173060 A1* | 8/2006 | Chang et al. ............. 514/389 |
| 2006/0183786 A1 | 8/2006 | Wang |
| 2006/0189944 A1 | 8/2006 | Campbell |
| 2006/0228391 A1 | 10/2006 | Seyedin |
| 2007/0004790 A1 | 1/2007 | Chow |
| 2007/0156180 A1 | 7/2007 | Jaax |
| 2007/0185497 A1 | 8/2007 | Cauthen |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos |
| 2007/0253994 A1 | 11/2007 | Hildebrand |
| 2008/0020076 A1 | 1/2008 | Jhamandas |
| 2008/0021074 A1 | 1/2008 | Cartt |
| 2008/0091207 A1 | 4/2008 | Truckai |
| 2008/0152709 A1 | 6/2008 | Bortz |
| 2008/0171075 A1 | 7/2008 | Ozturk et al. |

FOREIGN PATENT DOCUMENTS

| | | |
|---|---|---|
| WO | 2005034998 A2 | 4/2005 |
| WO | 2005110362 A1 | 11/2005 |
| WO | 2006011915 A1 | 2/2006 |
| WO | 2006022611 A2 | 3/2006 |
| WO | 2006101540 A1 | 9/2006 |
| WO | 2008014066 A1 | 1/2008 |
| WO | 2008079868 A1 | 7/2008 |
| WO | 2009100441 A2 | 8/2009 |

OTHER PUBLICATIONS

Moore, Daniel P., M.D., Helping Your Patients With Spasticity Reach Maximal Function, vol. 104, No. 2, Aug. 1998, Postgraduate Medicine.

* cited by examiner

ALPHA ADRENERGIC RECEPTOR AGONISTS FOR TREATMENT OF PAIN AND/OR INFLAMMATION

This application claims the benefit of the filing date of Provisional Application No. 61/046,201, filed Apr. 18, 2008, entitled "Clonidine Formulations In A Biodegradable Polymer Carrier" and the benefit of the filing date of Provisional Application No. 61/146,479, filed Jan. 22, 2009, entitled "Alpha Adrenergic Receptor Agonists For Treatment Of Pain And/Or Inflammation." These entire disclosures are hereby incorporated by reference into the present disclosure.

BACKGROUND

Pain is typically experienced when the free nerve endings of pain receptors are subject to mechanical, thermal, chemical or other noxious stimuli. These pain receptors can transmit signals along afferent neurons to the central nervous system and then to the brain. When a person feels pain, any one or more of a number of problems can be associated with this sensation, including but not limited to reduced function, reduced mobility, complication of sleep patterns, and decreased quality of life.

The causes of pain include but are not limited to inflammation, injury, disease, muscle stress, the onset of a neuropathic event or syndrome, and damage that can result from surgery or an adverse physical, chemical or thermal event or from infection by a biologic agent. When a tissue is damaged, a host of endogenous pain inducing substances, for example, bradykinin and histamine can be released from the injured tissue. The pain inducing substances can bind to receptors on the sensory nerve terminals and thereby initiate afferent pain signals. After activation of the primary sensory afferent neurons, the projection neurons may be activated. These neurons carry the signal via the spinothalamic tract to higher parts of the central nervous system.

One known class of pharmaceuticals to treat pain is the opioids. This class of compounds is well-recognized as being among the most effective type of drugs for controlling pain, such as post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Consequently, physicians typically limit the administration of opioids to within the first twenty-four hours post-surgery. Thus, it would be preferable to use non-narcotic drugs that deliver direct, localized pain control at a surgical site.

One drug class that is known to the medical profession is the alpha adrenergic receptor agonists. In general, the alpha-adrenergic receptors mediate excitatory and inhibitory functions: alpha-1 adrenergic receptors are typically excitatory post-synaptic receptors which generally mediate responses in the effector organ, while alpha-2 adrenergic receptors are located postsynaptically as well as presynaptically, where they inhibit release of neurotransmitters.

Examples of alpha adrenergic receptor agonists used clinically to treat different condition include clonidine, phenoxybenzamine and prazosin (for treatment of hypertension and opioid withdrawal), naphazoline (for nasal decongestion), UK-14,304 and p-aminoclonidine (for -glaucoma).

However, to date alpha adrenergic receptor agonists have not been widely appreciated as effective treatments for pain and/or inflammation. Thus, there is a need to develop alpha adrenergic receptor agonists to prevent, treat or reduce pain and/or inflammation.

SUMMARY

Novel compositions and methods are provided for effectively reducing, preventing, or treating unwanted pain and/or inflammation. The pain and/or inflammation may be reduced for extended periods of time.

In one embodiment, an implantable drug depot is provided useful for reducing, preventing or treating pain and/or inflammation in a patient in need of such treatment, the implantable drug depot comprising a therapeutically effective amount of an alpha adrenergic receptor agonist, the depot being implantable at a site beneath the skin to reduce, prevent or treat pain and inflammation, wherein the drug depot is capable of releasing an effective amount of the alpha adrenergic receptor agonist over a period of at least one day.

In another embodiment, a method of treating or preventing pain and/or inflammation in a patient in need of such treatment is provided, the method comprising administering one or more biodegradable drug depots comprising a therapeutically effective amount of alpha adrenergic receptor agonist to a target tissue site beneath the skin, wherein the drug depot releases an effective amount of the alpha adrenergic receptor agonist over a period of at least 1 day.

In one exemplary embodiment, a method of reducing pain and/or inflammation in a patient in need of such treatment is provided, the method comprising delivering one or more biodegradable drug depots comprising a therapeutically effective amount of an alpha-2 adrenergic receptor agonist to a target tissue site beneath the skin of the patient, wherein the drug depot releases an effective amount of the alpha-2-adrenergic receptor agonist over a period of at least 1 day.

In another exemplary embodiment, an implantable drug depot useful for reducing, preventing or treating pain and inflammation (e.g., from sciatica, spondilothesis, stenosis, etc.) in a patient is provided, the implantable drug depot comprising a therapeutically effective amount of an alpha adrenergic receptor agonist and a polymer; wherein the drug depot is implantable at a site beneath the skin to reduce, prevent or treat pain and/or inflammation, and the depot is capable of releasing (i) about 5% to about 20% of the alpha adrenergic receptor agonist relative to a total amount of the alpha adrenergic receptor agonist loaded in the drug depot over a first period of up to 48 hours and (ii) about 21% to about 99% of the alpha adrenergic receptor agonist relative to a total amount of the alpha adrenergic receptor agonist loaded in the drug depot over a subsequent period of up to 3 to 90 days or 6 months.

The compositions and methods provided may be used to reduce, prevent, or treat inflammation and/or pain, including but not limited to inflammation and/or pain that follows surgery, chronic inflammatory diseases, chronic inflammatory bowel disease, osteoarthritis, osteolysis, tendonitis, sciatica, herniated discs, stenosis, myopathy, spondilothesis, lower back pain, facet pain, carpal tunnel syndrome, tarsal tunnel syndrome, failed back pain or the like.

The pharmaceutical composition may for example, be part of a drug depot. The drug depot may: (i) consist of the alpha adrenergic receptor agonist and the biodegradable polymer(s); or (ii) consist essentially of the alpha adrenergic receptor agonist; or (iii) comprise the alpha adrenergic receptor agonist and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

In some embodiments, the drug depot comprises at least one biodegradable polymer in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, there is a pharmaceutical formulation comprising: an alpha adrenergic receptor agonist, wherein the alpha adrenergic receptor agonist comprises from about 0.1 wt. % to about 40 wt. % of the formulation, and at least one biodegradable polymer. In some embodiments, the alpha adrenergic receptor agonist comprises from about 0.5 wt. % to about 20 wt. %, about 3 wt. % to about 18 wt. %, about 5 wt. % to about 15 wt. % or about 7.5 wt. % to about 12.5 wt. % of the formulation.

In some embodiments, the drug depot provides a therapeutically effective dosage amount (e.g., alpha agonist) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months or 1 year or longer.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
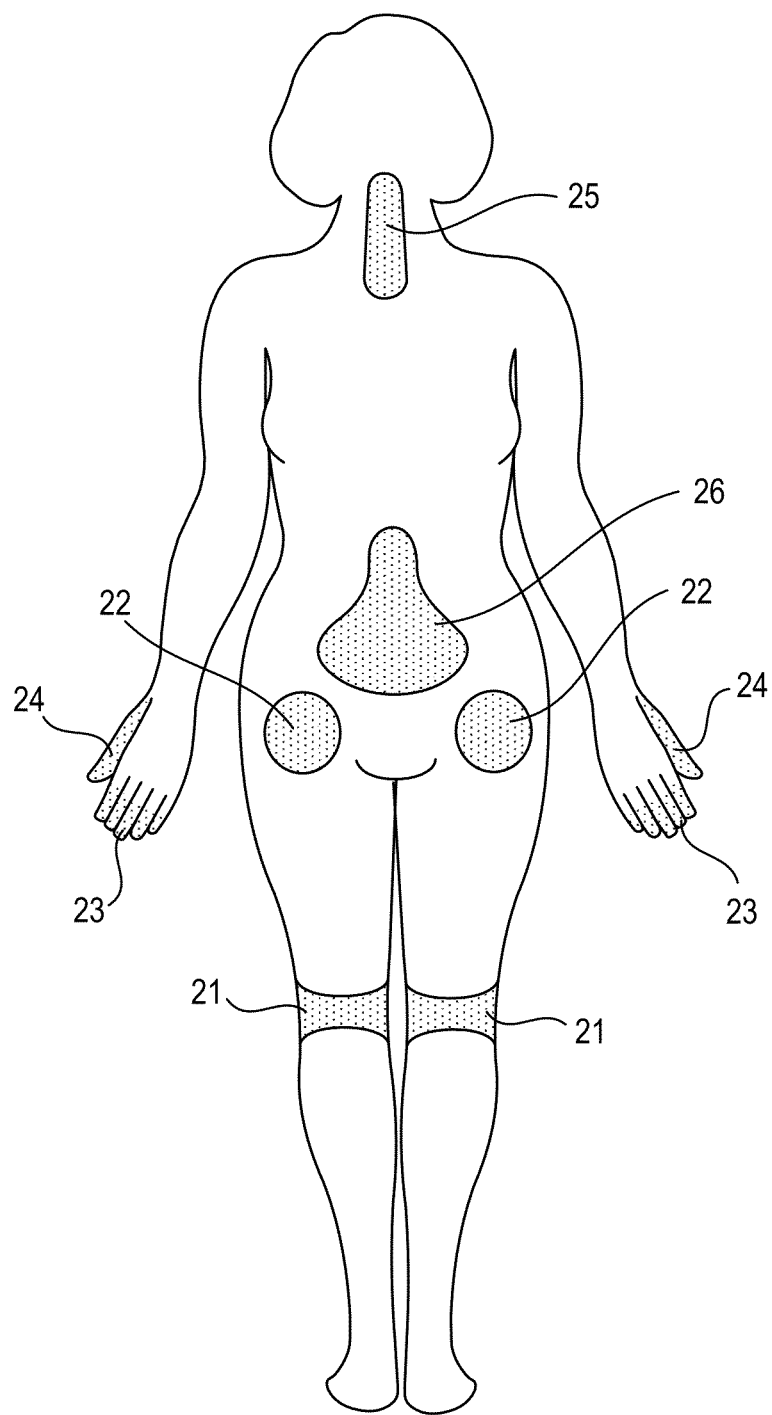
FIG. 1 illustrates a number of common locations within a patient that may be sites at which pain occurs and locations at which a drug depot containing an alpha adrenergic receptor agonist can locally be administered thereto.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

Alpha-Adrenergic Agonists

The methods and compositions of the present application utilize an alpha adrenergic agonist. Human adrenergic receptors are integral membrane proteins, which have been classified into two broad classes, the alpha and the beta adrenergic receptors.

Both types mediate the action of the peripheral sympathetic nervous system upon binding of catecholamines, norepinephrine and epinephrine. Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha-1, alpha-2, alpha-1/alpha-2 subtypes. Functional differences between alpha-1 and alpha-2 receptors have been recognized, and compounds, which exhibit selective binding between these two subtypes have been developed. Thus, in published international patent application WO 92/0073, the selective ability of the R(+) enantiomer of terazosin to selectively bind to adrenergic receptors of the alpha-1 subtype was reported. The alpha-1/alpha-2 selectivity of this compound was disclosed as being significant because stimulation of the alpha-2 receptors was said to inhibit secretion of epinephrine and norepinephrine, while antagonism of the alpha-2 receptor was said to increase secretion of these hormones. For a further general background on the alpha-adrenergic receptors, the reader's attention is directed to text known in the art such as for example Robert R. Ruffolo, Jr., alpha-Adrenoreceptors: Molecular Biology, Biochemistry and Pharmacology, (Progress in Basic and Clinical Pharmacology series, Karger, 1991). The cloning, sequencing and expression of alpha receptor subtypes from animal tissues has led to the subclassification of the alpha-1 adrenergic receptors into alpha-1A, alpha-1B, and alpha-1D. Similarly, the alpha-2 adrenergic receptors have also been classified alpha-2A, alpha-2B, and alpha-2C receptors based on their pharmacological and molecular characterization: alpha-2A/D (alpha-2A in human and alpha-2D in rat); alpha-2B; and alpha-2C (Bylund et al., Pharmacol. Rev. 46:121-136 (1994); and Hein and Kobilka, Neuropharmacol. 357-366 (1995)). The alpha-2A and alpha-2B subtypes can regulate arterial contraction in some vascular beds, and the alpha-2A and alpha-2C subtypes mediate feedback inhibition of norepinephrine release from sympathetic nerve endings. The alpha-2A subtype also mediates many of the central effects of alpha-2 adrenergic agonists (Calzada and Artinano, Pharmacol. Res. 44: 195-208 (2001); Hein et al., Ann. NY Acad. Science 881:265-271 (1999). Each alpha-2 receptor subtype appears to exhibit its own pharmacological and tissue specificities. Compounds having a degree of specificity for one or more of these subtypes may be more specific therapeutic agents for a given indication than, for example, an alpha-2 receptor pan-agonist (such as the drug clonidine).

The term "alpha adrenergic agonist" as used herein, refers to any compound that binds to and/or activates and/or agonizes at least one or more alpha-adrenergic receptor or its subtypes to any degree and/or stabilizes at least one or more alpha-adrenergic receptor or its subtypes in an active or inactive conformation. Thus, by the term alpha-adrenergic receptor agonist it is meant to include partial agonists, inverse agonists, as well as complete agonists of one or more alpha-adrenergic receptors or its subtypes.

The terms "alpha adrenergic receptor agonist" "alpha adrenergic agonist" and "alpha agonist" as used herein, are synonymous. An alpha adrenergic agonist may be a selective alpha-1 adrenergic agonist, a selective alpha-2 adrenergic agonist, or a mixed alpha-1/alpha-2 adrenergic agonist. The term "mixed alpha-1/alpha-2 agonist" as used herein, refers to a drug that activates both the alpha-1 receptor and the alpha-2 receptor including one or more of its subtypes. It may also be referred to as a non-selective alpha agonist.

It will be understood by those of ordinary skill in the art that selective alpha-2 agonists may weakly activate the alpha-1 receptor and the alpha-1 agonist may weakly activate the alpha-2 receptor but this weak activation will not be to any significant amount and thus the compound is still classified as a selective alpha-1 or alpha-2 agonist.

The term "activate" or grammatical variants thereof, as used herein, refers to binding to a receptor and causing the receptor to produce a cellular or physiological change. Agonist activation can be characterized using any of a variety of routine assays, including, for example, Receptor Selection and Amplification Technology (RSAT) assays (Messier et al., Pharmacol. Toxicol. 76:308-11 (1995); cyclic AMP assays (Shimizu et al., J. Neurochem. 16:1609-1619 (1969)); and cytosensor microphysiometry assays (Neve et al., J. Biol. Chem. 267:25748-25753 (1992)). For example, such assays generally are performed using cells that naturally express only a single alpha adrenergic receptor subtype, or using transfected cells expressing a single recombinant alpha-adrenergic receptor subtype. The adrenergic receptor can be a human receptor or homolog of a human receptor having a similar pharmacology. The RSAT assay measures receptor-mediated loss of contact inhibition resulting in selective proliferation of receptor-containing cells in a mixed population of confluent cells. The increase in cell number is assessed with an appropriate detectable marker gene such as beta-galactosidase, if desired, in a high throughput or ultra high throughput assay format. Receptors that activate the G protein, Gq, elicit the proliferative response. Alpha-adrenergic receptors, which normally couple to Gi, activate the RSAT response when coexpressed with a hybrid Gq protein containing a Gi receptor recognition domain, designated Gq/i5 (Conklin et al., Nature 363:274-6 (1993)).

In some embodiments, the alpha adrenergic receptor agonist comprises an alpha-1 adrenergic receptor agonist, which acts as an analgesic and/or anti-inflammatory agent. Alpha 1-adrenergic receptors are members of the G protein-coupled receptor superfamily. Upon activation, a heterotrimeric G protein, Gq, activates phospholipase C (PLC), which causes an increase in IP3 and calcium. This triggers the physiological effects. Examples of alpha-1 adrenergic receptor agonists include, but are in no way limited to methoxamine, methyl-norepinephrine, norepinephrine, metaraminol, oxymetazoline, xylometazoline, phenylephrine, 2-(anilinomethyl)imidazolines, synephrine, or a combination thereof.

In some embodiments, the alpha adrenergic receptor agonist comprises an alpha-2 adrenergic receptor agonist, which acts as an analgesic and/or anti-inflammatory agent. Examples of alpha-2 adrenergic receptor agonists useful in the present application include, but are in no way limited to L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, moxonidine, mivazerol, rilmenidine, UK 14,304, B-HT 933, B-HT 920, octopamine or a combination thereof.

Other alpha adrenergic agonists include, but are not limited to, amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

Exemplary alpha-2 adrenergic agonists that can be included in the drug depot comprise clonidine, p-aminoclonidine, guanabenz, lidamidine, tizanidine, moxonidine, methyldopa, xylazine, guanfacine, detomidine, medetomidine, dexmedetomidine or a combination thereof.

In one embodiment, the alpha adrenergic agonist can be used as a racemic mixture. In yet another embodiment, the alpha adrenergic agonist is used as a single stereoisomer. In another embodiment, the alpha adrenergic agonist is used as a mixture of stereo isomers containing equal (1:1) or unequal amounts of stereoisomers. For example, in some embodiments, the alpha adrenergic agonist may comprise mixtures of (+)R and (−) enantiomers of the agonist. In various embodiments, the alpha adrenergic agonist may comprise a 1:1 racemic mixture of the agonist.

The target tissue site chosen for alpha-agonist delivery depends on, among other things, upon the condition being treated, desired therapeutic concentration of the drug to be achieved in the patient and the duration of drug concentration that must be maintained.

In some embodiments, local administration of the drug depot at or near the target tissue site allows for a lower dose of the alpha adrenergic agonist to be used than the usual oral, intravenous, or intramuscular dose. For example, local administration of the drug depot can be accomplished with daily doses that are 20%, 15%, 10%, 5%, 1%, 0.5%, 0.1%, 0.01% of the usual oral, intravenous or intramuscular dose. In turn, systemic side effects, such as for example, liver transaminase elevations, hepatitis, liver failure, myopathy, constipation, etc. may be reduced or eliminated.

The concentration of alpha adrenergic receptor agonist (e.g., alpha-1, alpha-2, alpha-1 and alpha-2) included in the drug depot and used in the methodologies described herein is a concentration effective to produce a therapeutic effect of preventing, treating or reducing pain and/or inflammation. Dosages of alpha adrenergic receptor agonist, e.g., clonidine for producing an analgesic effect in human patients upon local administration can typically range in some embodiments from between about 150 micrograms to 800 micrograms per day or from 3-12 micrograms/hour by local infusion.

However, as will be understood by the skilled artisan upon reading this disclosure, the effective concentration will vary depending upon the alpha adrenergic receptor agonist selected, the route of administration, the frequency of administration, the formulation administered, and the condition being treated.

In one embodiment, the alpha adrenergic agonist is administered in an amount of about 0.0001 mg/kg/day to about 40 mg/kg/day. In another embodiment, the alpha adrenergic agonist is administered in an amount of about 0.001 mg/kg/day to about 4 mg/kg/day. In one embodiment, the alpha adrenergic agonist is administered in an amount of about 0.01 mg/kg/day to about 0.4 mg/kg/day.

In one embodiment, the one or more alpha adrenergic agonists can be administered in a drug depot, which also contains another anti-inflammatory and/or an analgesic. By including one or more alpha adrenergic agonists in the drug depot, this can enhance the effect of the analgesic and/or anti-inflammatory. In one embodiment, "enhanced effect" means that, when co-administered with an alpha adrenergic agonist, lower doses of the selected analgesic and/or anti-inflammatory agent may be required to achieve the same analgesic effect as when the analgesic and/or anti-inflammatory is administered alone or greater analgesic or anti-inflammatory effect is achieved when usual doses of the selected analgesic and/or anti-inflammatory is administered with an alpha adrenergic agonist.

Analgesic refers to an agent or compound that can reduce, relieve or eliminate pain. In addition to the alpha adrenergic agonist, examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papavereturn, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. In addition to the alpha adrenergic agonist, examples of anti-inflammatory agents include, but are not limited to, a statin, sulindac, sulfasalazine, guanidinoethyldisulfide, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketorolac, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluocinolone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; sulfasalazine, sulindac, tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to an alpha adrenergic receptor agonist or alpha agonist (e.g., alpha-2 agonist, alpha-2 selective agonist, alpha-1 selective agonist, alpha-1/alpha-2 mixed or non-selective agonist, etc.), the inventor is also referring to a pharmaceutically acceptable salt of the alpha adrenergic receptor agonist including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

A "drug depot" is the composition in which at least one alpha adrenergic receptor agonist is administered to the body. Thus, a drug depot may comprise a physical structure to facilitate implantation and retention in a desired site (e.g., a disc space, a spinal canal, a tissue of the patient, particularly at or near a site of surgery, or other site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 mm to about 5 cm from the implant site, and comprises at least one alpha adrenergic receptor agonist or its pharmaceutically acceptable salt.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, fiber, strip, sheet or other pharmaceutical delivery compositions or a combination thereof. The drug depot may comprise a pump that holds and administers the pharmaceutical. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In various embodiments, the drug depot may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof.

The drug depot may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Typically, the non-degradable drug depots may need to be removed.

A "therapeutically effective amount" or "effective amount" is such that when administered, the drug results in alteration of the biological activity, such as, for example, inhibition of inflammation, reduction or alleviation of pain, improvement in the condition through muscle relaxation, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, sheets, pellets, microparticles, microspheres, microcapsules, spheroids, shaped derivatives or paste. The formulations may be in a form that is suitable for suspension in isotonic saline, physiological buffer or other solution acceptable for injection into a patient. Further, the formulations may be used in conjunction with any implantable, insertable or injectable system that a person of ordinary skill would appreciate as useful in connection with embodiments herein including but not limited to parenteral formulations, microspheres, microcapsules, gels, pastes, implantable rods, pellets, plates or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 hour.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The phrase "release rate profile" refers to the percentage of active ingredient that is released over fixed units of time, e.g., mcg/hr, mcg/day, mg/hr, mg/day, 10% per day for ten days, etc. As persons of ordinary skill know, a release rate profile may be but need not be linear. By way of a non-limiting example, the drug depot may be a pellet that releases at least one alpha agonist over a period of time.

Treating or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation. By way of example, the administration of the effective dosage alpha adrenergic receptor agonist may be used to prevent, treat or relieve the symptoms of pain and/or inflammation for different diseases or conditions. These disease/conditions may comprise chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, tissue transplant rejection, graft versus host disease and atopic conditions, such as asthma and allergy, including allergic rhinitis, gastrointestinal allergies, including food allergies, eosinophilia, conjunctivitis or glomerular nephritis.

One chronic condition is sciatica. In general, sciatica" is an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the alpha adrenergic agonist may be used to reduce, treat, or prevent sciatic pain and/or inflammation by locally administering the alpha adrenergic agonist at one or more target tissue sites (e.g., nerve root, dorsal root ganglion, focal sites of pain, at or near the spinal column, etc.).

"Localized" delivery includes delivery where one or more drugs are deposited within a tissue, for example, a nerve root of the nervous system or a region of the brain, or in close proximity (within about 10 cm, or within about 5 cm, or within 0.1 cm for example) thereto. A "targeted delivery system" provides delivery of one or more drugs depots, gels or depot dispersed in the gel having a quantity of therapeutic agent that can be deposited at or near the target site as needed for treatment of pain, inflammation or other disease or condition.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrase "pain management medication" includes one or more therapeutic agents that are administered to prevent, alleviate or remove pain entirely. These include one or more alpha adrenergic agonists alone or in combination with an anti-inflammatory agent, muscle relaxant, analgesic, anesthetic, narcotic, or so forth, or combinations thereof.

In various embodiments, the depot can be designed to cause an initial burst dose of therapeutic agent within the first 24 hours, 2 days, 3 days, 4 days, or 5 days after implantation. "Initial burst" or "burst effect" or "bolus dose" refer to the release of therapeutic agent from the depot during the first 24 hours, 2 days, 3 days, 4 days, or 5 days after the depot comes in contact with an aqueous fluid (e.g., synovial fluid, cerebral spinal fluid, etc.). This burst effect is particularly beneficial for the analgesic, while in various embodiments, for the anti-inflammatory agent a more linear release of a longer duration may be desired. The "burst effect" is believed to be due to the increased release of therapeutic agent from the depot. In alternative embodiments, the depot (e.g., gel, pellet, wafer, etc.) is designed to avoid this initial burst effect.

The drug depot comprising at least one alpha-2 adrenergic agonist or its pharmaceutically acceptable salt may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one alpha adrenergic agonist or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered with the alpha adrenergic agonist include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, or antioxidants, such as dilhiocarbamate.

Specific examples of additional therapeutic agents suitable for use include, but are not limited to, an anabolic growth factor or anti-catabolic growth factor, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

In addition to the alpha agonist, suitable analgesic agents include, but are not limited to, acetaminophen, bupivacaine, tramadol, opioid analgesics such as amitriptyline, carbamazepine, gabapentin, pregabalin, opioid analgesics or a combination thereof. Opioid analgesics include, alfentanil, allyl-prodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol or a combination thereof.

For each alpha adrenergic agonist, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

The therapeutic agent (e.g., alpha agonist, muscle relaxant, steroid, etc.) also includes its pharmaceutically acceptable salt. As used herein, "pharmaceutically acceptable salts" refer to derivatives of the disclosed compounds (e.g., esters or amines) wherein the parent compound may be modified by making acidic or basic salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, or nitric acids; or the salts prepared from organic acids such as acetic, fuoric, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid. Pharmaceutically acceptable also includes the racemic mixtures ((+)-R and (−)-S enantiomers) or each of the dextro and levo isomers of the therapeutic agent individually. The therapeutic agent may be in the free acid or base form or be pegylated for long acting activity.

Medetomidine/Dexmedetomidine/Tizanidine/Romifidine

In some embodiments, the drug depot comprises the alpha agonist medetomidine, dexmedetomidine, tizanidine, romifidine or combinations thereof. When referring to these compounds, unless otherwise specified or apparent from context it is understood that the inventor is also referring to pharmaceutically acceptable salts, racemates, enantiomers, amides, or esters thereof. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrochloric, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

In some embodiments, the medetomidine, dexmedetomidine, tizanidine, or romifidine may not only be in the salt form, but may be in the base form (e.g., free base). The dosage may be from approximately 0.0005 to approximately 15,000 µg/day. Additional dosages of medetomidine, dexmedetomidine, tizanidine, or romifidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of medetomidine, dexmedetomidine, tizanidine, or romifidine may be from approximately 0.005 to approximately 15 µg/day. In another embodiment, the dosage of medetomidine, dexmedetomidine, tizanidine, or romifidine may be from approximately 0.005 to approximately 10 µg/day. In another embodiment, the dosage of medetomidine, dexmedetomidine, tizanidine, or romifidine may be from approximately 0.005 to approximately 5 µg/day. In another embodiment, the dosage of medetomidine, dexmedetomidine, tizanidine, or romifidine is from approximately 0.005 to 2.5 µg/day. In some embodiments, the amount of medetomidine, dexmedetomidine, tizanidine, or romifidine is between 40 and 600 µg/day. In some embodiments, the amount of medetomidine, dexmedetomidine, tizanidine, or romifidine is between 200 and 400 µg/day.

Xylazine/Guanfacine/Guanabenz

In some embodiments, the drug depot comprises the alpha agonist xylazine, guanfacine, guanabenz, or combinations thereof. When referring to these compounds, unless otherwise specified or apparent from context it is understood that the inventor is also referring to pharmaceutically acceptable salts, racemates, enantiomers, amides, or esters thereof. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrochloric, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

The dosage of the xylazine, guanfacine, or guanabenz may be from 0.0001 mg to 5000 mg per day. For example, the dosage of xylazine, guanfacine, or guanabenz may include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In some embodiments, the dosage of xylazine, guanfacine, or guanabenz may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, 250 mg, 300 mg, 350 mg, 400 mg, 450 mg, or 500 mg of xylazine, guanfacine, or guanabenz per day.

Oxymetazoline

In some embodiments, the drug depot comprises the alpha 1 agonist oxymetazoline. When referring to oxymetazoline, unless otherwise specified or apparent from context it is understood that the inventor is also referring to pharmaceutically acceptable salts, racemates, enantiomers, amides, or esters thereof. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrochloric, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

In some embodiments, the oxymetazoline may not only be in the salt form, but may be in the base form (e.g., free base). The dosage may be from approximately 0.0005 to approximately 15,000 µg/day. Additional dosages of may be from 0.1 mg to 5000 mg per day. For example, the dosage of oxymetazoline may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, 250 mg, 300 mg, 350 mg, 400 mg, 450 mg, or 500 mg of oxymetazoline per day.

Phenylephrine

In some embodiments, the drug depot comprises the alpha 1 agonist phenylephrine. When referring to phenylephrine, unless otherwise specified or apparent from context it is understood that the inventor is also referring to pharmaceutically acceptable salts, racemates, enantiomers, amides, or esters thereof. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrochloric, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

In some embodiments, the phenylephrine may not only be in the salt form, but may be in the base form (e.g., free base). The dosage may be from approximately 0.0005 to approximately 15,000 µg/day. Additional dosages of may be from 0.1 mg to 5000 mg per day. For example, the dosage of phenylephrine may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, 250 mg, 300 mg, 350 mg, 400 mg, 450 mg, or 500 mg of phenylephrine per day.

Clonidine

When referring to clonidine, unless otherwise specified or apparent from context it is understood that the inventor is also referring to pharmaceutically acceptable salts. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to clonidine the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non limiting example, when formulating clonidine with poly(orthoesters) it may be desirable to use the clonidine base formulation. By contrast, when formulating clonidine with PLGA, it may be desirable to use the HCl salt form.

In one embodiment, the alpha adrenergic agonist is an alpha-2 adrenergic agonist comprising clonidine, also referred to as 2,6-dichloro-N-2-imidazolidinyldenebenzenamine. Clonidine or a pharmaceutically acceptable salt thereof is available from various pharmaceutical manufactures.

The dosage may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

In various embodiments, there is a pharmaceutical formulation comprising: clonidine, wherein the clonidine comprises from about 1 wt. % to about 20 wt. % of the formulation, and at least one biodegradable polymer. In some embodiments, the pharmaceutical the clonidine comprises from about 3 wt. % to about 20 wt. %, about 3 wt. % to about 18 wt. %, about 5 wt. % to about 15 wt. % or about 7.5 wt. % to about 12.5 wt. % of the formulation. By way of example, when using a 5%-15% clonidine composition, the mole ratio of clonidine to polymer would be from approximately 16-52 when using an approximately 80 kDalton polymer that has a 267 grams/mole ratio.

In some embodiments, the at least one biodegradable polymer comprises poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, there is a pharmaceutical formulation comprising clonidine, wherein the clonidine is in a mixture of clonidine hydrochloride and clonidine base and the mixture comprises from about 0.1 wt. % to about 30 wt. % of the formulation and a polymer comprises at least 70% of the formulation. In some embodiments, the polymer in this formulation is polyorthoester.

In various embodiments, the drug particle size is from about 5 to 30 micrometers, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the clonidine are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, there is a pharmaceutical formulation comprising: clonidine, wherein the clonidine is in the form of a hydrochloride salt, and comprises from about 1 wt. % to about 20 wt. % of the formulation, and at least one biodegradable polymer, wherein the at least one biodegradable polymer comprises poly(lactide-co-glycolide) (or poly (lactic-co-glycolic acid)) or poly(orthoester) or a combination thereof, and said at least one biodegradable polymer comprises at least 80 wt. % of said formulation.

In some embodiments, there are methods for treating acute pain. These methods comprise: administering a pharmaceutical composition to an organism, wherein said pharmaceutical composition comprises from about 1 wt. % to about 20 wt. % of the formulation, and at least one biodegradable polymer. In some embodiments, the loading is from about 5 wt. % to about 10 wt. %. In some embodiments, the loading is from about 10 wt. % to about 20 wt. %.

In some embodiments, there is a higher loading of clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

In some embodiments, the drug depot contains excipients along with the clonidine. Exemplary excipients that may be formulated with clonidine in addition to the biodegradable polymer include but are not limited to MgO (e.g., 1 wt. %), 5050 DLG 6E, 5050 DLG 1A, mPEG, TBO-Ac, mPEG, Span-65, Span-85, pluronic F127, TBO-Ac, sorbital, cyclodextrin, maltodextrin, pluronic F68, CaCl, 5050 7A and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as using a mortar and pestle, jet-drying or jet milling.

In some embodiments, clonidine is released at a rate of 2-3 µg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a biopolymer are implanted into a person at or near a target tissue site. If clonidine is implanted at multiple sites that triangulate the target site then in some embodiments, the total amount of clonidine at each site is a fraction of the total 300-425 micrograms. For example, one may implant a single dose of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

In some embodiments, there is a drug depot comprising clonidine or clonidine hydrochloride and a polymer, wherein the polymer is one more of various embodiments, the drug depot comprises poly(lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone or a combination thereof.

In one exemplary dosing regimen, a rat may be provided with sufficient clonidine in a biodegradable polymer to provide sustain release of 0.240 µg/day for 135 days. The total amount of clonidine that is administered over this time period would be approximately 32.4 µg. In another exemplary dosing regimen, a human is provided with sufficient clonidine in a biodegradable polymer to provide sustain release of 2.4 µg/day for 135 days. The total amount of clonidine that is administered over this time period would be approximately 324 µg.

When using a plurality of pellets, the pellet number is based on the amount of drug loading into a pellet of appropriate size (i.e., 0.5 mm diameter×4 mm length) and how much drug is needed (e.g., approximately 325 µg clonidine (3 pellets)). In some embodiments there is a polymer that releases a bolus amount of compound over the first few (~5) days before it settles down and releases 2.5 mg/day for 135 days. An exemplary formulation is 5% wt. clonidine, 100 DL 5E.

In some embodiments, the polymer depots of present application enable one to provide efficacy of the active ingredient that is equivalent to subcutaneous injections that deliver more than 2.5 times as much drug.

Fluocinolone

In one embodiment, in addition to the alpha agonist, the anti-inflammatory agent comprises fluocinolone or a pharmaceutically acceptable salt thereof such as the acetonide salt. Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.0005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and approximately 0.002 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day.

Dexamethasone

In one embodiment of the present invention, in addition to the alpha agonist, the anti-inflammatory agent is dexamethasone free base or dexamethasone acetate, also referred to as 8S,9R,10S,11S,13S,14S,16R,17R)-9-Fluoro-11,17-dihydroxy-17-(2-hydroxyacetyl)-10,13,16-trimethyl-6,7,8,11, 12,14,15,16 octahydrocyclopenta[a]-phenanthren-3-one), or a pharmaceutically acceptable salt thereof, which is available from various manufacturers.

In various embodiments, dexamethasone may be released from the depot at a dose of about 10 pg to about 80 mg/day, about 2.4 ng/day to about 50 mg/day, about 50 ng/day to about 2.5 mg/day, about 250 ng/day to about 250 ug/day, about 250 ng/day to about 50 ug/day, about 250 ng/day to about 25 ug/day, about 250 ng/day to about 1 ug/day, about 300 ng/day to about 750 ng/day or about 0.50 ug/day. In various embodiments, the dose may be about 0.01 to about 10 µg/day or about 1 ng to about 120 µg/day.

In one exemplary embodiment, the dexamethasone is dexamethasone sodium phosphate.

GED

In one embodiment, in addition to the alpha agonist, the therapeutic agent is GED (guanidinoethyldisulfide), which is an inducible nitric oxide synthase inhibitor having anti-inflammatory properties. GED may be in its hydrogen carbonate salt form.

The dosage of GED may be from approximately 0.0005 µg/day to approximately 100 mg/day. Additional dosages of GED include from approximately 0.0005 µg/day to approximately 50 mg/day; approximately 0.0005 µg/day to approximately 10 mg/day; approximately 0.0005 µg/day to approximately 1 mg/day; approximately 0.0005 to approximately 800 µg/day; approximately 0.0005 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; and approximately 0.0025 to approximately 15 µg/day. In another embodiment, the dosage of GED is from approximately 0.005 to approximately 15 µg/day. In another embodiment, the dosage of GED is from approximately 0.005 to approximately 10 µg/day. In another embodiment, the dosage of GED is from approximately 0.005 to approximately 5 µg/day. In another embodiment, the dosage of GED is from approximately 0.005 to 2.5 µg/day. In some embodiments, the amount of GED is between 40 and 600 µg/day. In some embodiments, the amount of GED is between 200 and 400 µg/day.

In one exemplary embodiment the dosage of GED is between 0.5 and 4 mg/day. In another exemplary embodiment the dosage of GED is between 0.75 and 3.5 mg/day.

Lovastatin

In one exemplary embodiment, in addition to the alpha-agonist, the anti-inflammatory agent comprises lovastatin. Lovastatin is a statin that may be obtained from various manufacturers in various forms (e.g., injection, powder, etc.). For example, lovastatin may be obtained from Merck as Mevacor® (see U.S. Pat. No. 4,231,938, the entire disclosure is herein incorporated by reference). Suitable pharmaceutically acceptable salts of lovastatin include one or more compounds derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of lovastatin include lithium, calcium, hemicalcium, sodium, potassium, magnesium, aluminum, ferrous or ferric salts thereof or a combination thereof.

In various embodiments, the therapeutically effective amount of lovastatin comprises from about 0.1 pg to about 2000 mg, for example, 0.1 ng to 1000 mg, 500 mg, 100 mg, 50 mg, 25 mg, 10 mg, 1 mg, 50 µg, 25 µg, 10 µg, 1 µg, 500 ng, 250 ng, 100 ng, 75 ng, 50 ng, 25 ng, 15 ng, 10 ng, 5 ng, or 1 ng of lovastatin per day. In various embodiments, the dosage may be, for example from about 3 ng/day to 0.3 µg/day.

Morphine

In one embodiment of the present invention, in addition to the alpha agonist, the analgesic agent is morphine. Morphine is also referred to as (5α,6α)-7,8-didehydro-4,5-epoxy-17-methylmorphinan-3,6-diol and has the chemical formula $C_{17}H_{19}NO_3$. Morphine and a pharmaceutically acceptable salt thereof is available from various manufacturers. In one exemplary embodiment, the morphine comprises morphine sulfate or hydrochloride.

The dosage of the morphine may be from 0.1 mg to 1000 mg per day. For example, the dosage of morphine may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg of morphine per day.

Tramadol

In one embodiment, in addition to the alpha agonist, the analgesic agent is tramadol. Tramadol is also referred to as (±)cis-2-[(dimethylamino)methyl]-1-(3-methoxyphenyl) cyclohexanol hydrochloride and has the chemical formula $C_{16}H_{25}NO_2$. Tramadol or a pharmaceutically acceptable salt thereof is available from various manufacturers. In various embodiments, tramadol HCL was used.

The dosage of the tramadol may be from 0.01 mg to 500 mg per day. For example, the dosage of tramadol may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, or 500 mg of tramadol per day.

In one embodiment, the drug depot contains sufficient tramadol to release between 2.5 and 30 mg/kg/day. In another embodiment the drug depot contains sufficient tramadol to release between 3 and 27.5 mg/kg/day.

The alpha adrenergic agonist may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).
Biodegradable In various embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed.

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

Where different combinations of polymers are used (bi, tri (e.g., PLGA-PEO-PLGA) or terpolymers) in the depot, they may be used in different molar ratios, 1:1, 2:1, 3:1, 4:1, 5:1, 6:1, 7:1, 8:1, 9:1, or 10:1. In various embodiments, for the 130 day release, the depot comprises 50:50 PLGA to 100 PLA. The molecular weight range is 0.45 to 0.8 dl/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

In some embodiments, the at least one biodegradable polymer comprises poly(lactic-co-glycolic acid) (PLA) or poly(orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In various embodiments, the drug depot comprises poly (lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, glycolide-caprolactone or a combination thereof.

In various embodiments, the depot may comprise of a biodegradeable polyorthoester. The mechanism of the degradation process of the polyorthoester can be hydrolytical or enzymatical in nature, or both. In various embodiments, the degradation can occur either at the surface (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., lauryl, methyl or ethyl ester end groups).

Additionally, by varying the comonomer ratio of the various monomers that form a polymer (e.g., the L/G/CL or G/CL ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L (CL refers to caprolactone, G refers to glycolic acid and L refers to lactic acid) with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the at least one alpha agonist are the only components of the pharmaceutical formulation.

In some embodiments, at least 75% of the particles have a size from about 1 micrometer to about 200 micrometers. In some embodiments, at least 85% of the particles have a size from about 1 micrometer to about 100 micrometers. In some embodiments, at least 95% of the particles have a size from about 5 micrometer to about 50 micrometers. In some embodiments, all of the particles have a size from about 10 micrometer to about 50 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a pellet, a sphere, a cylinder such as a rod or fiber, a flat surface such as a disc, film or sheet or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

In various embodiments, when the drug depot comprises a pellet, it may be placed at the incision site before the site is closed. The pellet may for example be made of thermoplastic materials. Additionally, specific materials that may be advantageous for use in the pellet include but are not limited to the compounds identified above as sustained release biopolymers. The drug depot may be formed by mixing the at least one alpha adrenergic agonist with the polymer.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium phosphate, and/or metal beads or particles. In various embodiments, the radiographic marker could be a spherical shape or a ring around the depot.

Gel

In various embodiments, the gel has a pre-dosed viscosity in the range of about 1 to about 2000 centipoise (cps), 1 to about 500 cps, 1 to about 200 cps, or 1 to about 100 cps. After the gel is administered to the target site, the viscosity of the gel will increase and the gel will have a modulus of elasticity (Young's modulus) in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot is provided that contains an adherent gel comprising at least one alpha adrenergic agonist that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times 10^2$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances.

In various embodiments, the molecular weight of the gel can be varied by any one of the many methods known in the art. The choice of method to vary molecular weight is typically determined by the composition of the gel (e.g., polymer versus non-polymer). For example in various embodiments, when the gel comprises one or more polymers, the degree of polymerization can be controlled by varying the amount of polymer initiators (e.g., benzoyl peroxide), organic solvents or activator (e.g. DMPT), crosslinking agents, polymerization agent, incorporation of chain transfer or chain capping agents, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

When the gel is designed to be a flowable gel, it can vary from low viscosity, similar to that of water, to a high viscosity, similar to that of a paste, depending on the molecular weight and concentration of the polymer used in the gel. The viscosity of the gel can be varied such that the polymeric composition can be applied to a patient's tissues by any convenient technique, for example, by brushing, spraying, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as, for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agents into the gel, microspheres may be dispersed within the gel, the microspheres being loaded with at least one analgesic agent and at least one anti-inflammatory agent. In one embodiment, the microspheres provide for a sustained release of the at least one alpha-2 adrenergic agonist. In yet another embodiment, the gel, which is biodegradable, prevents the microspheres from releasing the at least one alpha adrenergic agonist; the microspheres thus do not release the at least one alpha adrenergic agonist until it has been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the at least one alpha adrenergic agonist. The alpha adrenergic agonist may be placed into separate microspheres and then the microspheres combined, or the active ingredients can first be combined and then placed into the microspheres together.

Microspheres, much like a fluid, may disperse relatively quickly, depending upon the surrounding tissue type, and hence disperse the at least one analgesic agent and at least one anti-inflammatory agent. In some embodiments, the diameter of the microspheres range from about 10 microns in diameter to about 200 microns in diameter. In some embodiments they range from about 20 to 120 microns in diameters. Methods for making microspheres include but are not limited to solvent evaporation, phase separation and fluidized bed coating. In some situations, this may be desirable; in others, it may be more desirable to keep the at least one analgesic agent and at least one anti-inflammatory agent tightly constrained to a well-defined target site.

The present invention also contemplates the use of adherent gels to so constrain dispersal of the therapeutic agent. These gels may be deployed, for example, in a disc space, in a spinal canal, or in surrounding tissue.

Cannulas and Needles

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

Sterilization

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

Kits

In various embodiments, a kit is provided that may include additional parts along with the drug depot and/or medical device combined together to be used to implant the drug depot (e.g., pellet). The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include the agent for radiographic imaging. Each tool may be separately packaged in a plastic pouch that is radiation sterilized. A cover of the kit may include illustrations of the implanting procedure and a clear plastic cover may be placed over the compartments to maintain sterility.

Administration

In various embodiments, the alpha adrenergic agonist may be parenterally administered. The term "parenteral" as used herein refers to modes of administration, which bypass the gastrointestinal tract, and include for example, localized intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof.

Parenteral administration may additionally include, for example, an infusion pump that locally administers a pharmaceutical composition (e.g., alpha adrenergic agonist) through a catheter near the spine or one or more inflamed joints, an implantable mini-pump that can be inserted at or near the target site, an implantable controlled release device or sustained release delivery system that can release a certain amount of the composition continuously per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Potential drug delivery devices suitable for adaptation for the methods described herein include but are not limited to those described, for example, in U.S. Pat. No. 6,551,290 (assigned to Medtronic, the entire disclosure is herein incorporated by reference), which describes a medical catheter for target specific drug delivery; U.S. Pat. No. 6,571,125 (assigned to Medtronic, the entire disclosure is herein incorporated by reference), which describes an implantable medical device for controllably releasing a biologically active agent; U.S. Pat. No. 6,594,880 (assigned to Medtronic, the entire disclosure is herein incorporated by reference), which describes an intraparenchymal infusion catheter system for delivering therapeutic agents to selected sites in an organism; and U.S. Pat. No. 5,752,930 (assigned to Medtronic, the entire disclosure is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, light-weight devices for delivering liquid medication, implantable microminiature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates, and durations suitable for use in the described methods. In various embodiments, a method for delivering a therapeutic agent into a surgery site of a patient is provided. For example, the implantable Alzet® osmotic pump delivers the alpha agonist locally to the target tissue site on a continuous basis (e.g., the Alzet® osmotic pump allows a continuous infusion in microgram/hr delivery of the alpha agonist intrathecally near the sciatic).

The method of the present application comprises inserting a cannula at or near a target tissue site and implanting the drug depot at the target site beneath the skin of the patient and brushing, dripping, spraying, injecting, or painting the gel in the target site to hold or have the drug depot adhere to the target site. In this way unwanted migration of the drug depot away from the target site is reduced or eliminated.

In various embodiments, because the alpha adrenergic agonist is locally administered, therapeutically effective doses may be less than doses administered by other routes (oral, topical, etc.). For example, the drug dose delivered from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

In various embodiments, to administer the gel having the drug depot dispersed therein to the desired site, first the cannula or needle can be inserted through the skin and soft tissue down to the target tissue site and the gel administered (e.g., brushed, dripped, injected, or painted, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

FIG. 1 illustrates a number of common locations within a patient that may be sites at which inflammation and/or pain may occur. It will be recognized that the locations illustrated in FIG. 1 are merely exemplary of the many different locations within a patient that may be the sites of inflammation and/or pain. For example, inflammation and/or pain may occur at a patient's knees 21, hips 22, fingers 23, thumbs 24, neck 25, and spine 26.

Figure 2:
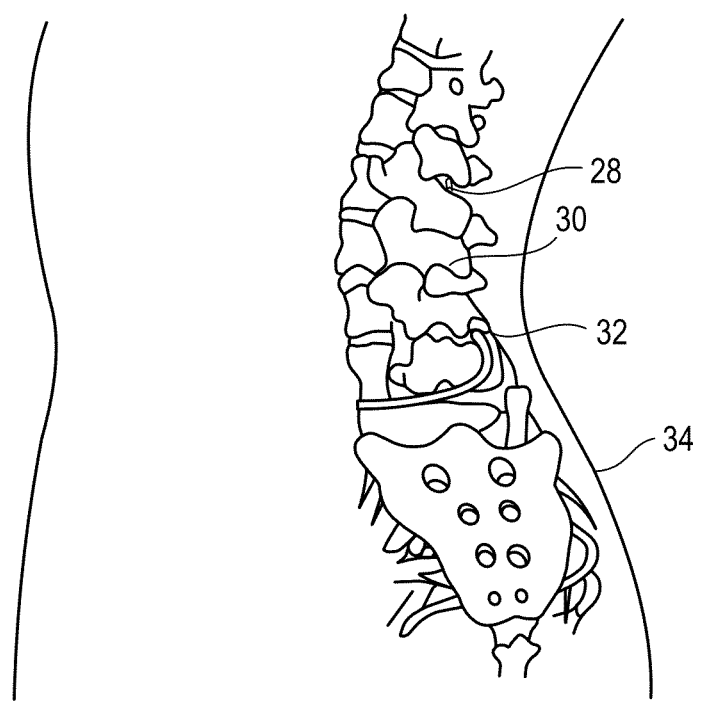
FIG. 2 illustrates a schematic dorsal view of the spine and sites at which a drug depot containing an alpha adrenergic receptor agonist can locally be administered thereto.

One exemplary embodiment where the depot is suitable for use in pain management due to inflammation is illustrated in FIG. 2. Schematically shown in FIG. 2 is a dorsal view of the spine 30 and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

The at least one alpha adrenergic agonist formulation may be used to form different pharmaceutical preparations (e.g., drug depots, injectable formulations, etc.). The pharmaceutical preparations may be formed in and administered with a suitable pharmaceutical carrier that may be solid or liquid, and placed in the appropriate form for parenteral or other administration as desired. As persons of ordinary skill are aware, known carriers include but are not limited to water, saline solution, gelatin, lactose, starches, stearic acid, magnesium stearate, sicaryl alcohol, talc, vegetable oils, benzyl alcohols, gums, waxes, propylene glycol, polyalkylene glycols and other known carriers.

Another embodiment provides a method for treating a mammal suffering from pain and/or inflammation, said method comprising administering a therapeutically effective amount of at least one alpha adrenergic agonist at a target site beneath the skin at or near the target site. The at least one alpha adrenergic agonist may for example be administered locally to the target tissue site as a drug depot.

In some embodiments, the therapeutically effective dosage amount (e.g., alpha adrenergic agonist dose) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 150 days, or 3 days to 6 months.

In some embodiments, the at least one alpha adrenergic agonist or a portion of the at least one alpha adrenergic agonist is administered as a bolus dose at the target tissue to provide an immediate release of the alpha adrenergic agonist.

In some embodiments there is a composition useful for the treatment of inflammation comprising an effective amount of at least one alpha adrenergic agonist that is capable of being locally administered to a target tissue site. By way of example, they may be administered locally to the foraminal spine, the epidural space or the intrathecal space of a spinal cord. Exemplary administration routes include but are not limited to catheter drug pumps, one or more local injections, polymer releases and combinations thereof.

In some embodiments, the at least one alpha adrenergic agonist is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the alpha adrenergic agonist is administered by placement into an open patient cavity during surgery.

In some embodiments, the formulation is implantable into a surgical site at the time of surgery. The active ingredients may then be released from the depot via diffusion in a sustained fashion over a period of time, e.g., 3-15 days, 5-10 days or 7-10 days post surgery in order to address pain and inflammation. In some embodiments, the active ingredient may provide longer duration of pain and/or inflammation relief for chronic diseases/conditions as discussed above with release of one or more drugs up to 6 months or 1 year (e.g., 90, 100, 135, 150, 180 days or longer).

In some embodiments, the drug depot may release 5%, 10%, 15%, 20%, 25%, 30%, 40%, 50%, 60%, 70%, 80%, 90%, 95%, or 99% of the at least one alpha adrenergic agonist or pharmaceutically acceptable salt thereof relative to a total amount of at least one alpha adrenergic agonist loaded in the drug depot over a period of 3 to 12 days, 5 to 10 days or 7 to 10 days after the drug depot is administered to the target tissue site. In some embodiments, the active ingredient may provide longer duration of pain and/or inflammation relief for chronic diseases/conditions as discussed above with release of one or more drugs up to 6 months or 1 year (e.g., 90, 100, 135, 150, 180 days or longer).

In various embodiments, an implantable drug depot useful for reducing, preventing or treating pain and/or inflammation is provided in a patient in need of such treatment, the implantable drug depot comprising a therapeutically effective amount of a alpha adrenergic agonist or pharmaceutically acceptable salts thereof, the depot being implantable at a site beneath the skin to reduce, prevent or treat pain and/or inflammation, wherein the drug depot (i) comprises one or more immediate release layer(s) that is capable of releasing about 5% to about 20% of the alpha adrenergic agonist or pharmaceutically acceptable salts thereof relative to a total amount of the alpha adrenergic agonist or pharmaceutically acceptable salt thereof loaded in the drug depot over a first period of up to 48 hours and (ii) one or more sustain release layer(s) that is capable of releasing about 21% to about 99% of the alpha adrenergic agonist or pharmaceutically acceptable salt thereof relative to a total amount of the alpha adrenergic agonist or pharmaceutically acceptable salt thereof loaded in the drug depot over a subsequent period of up to 3 days to 6 months.

By way of a non-limiting example, the target tissue site may comprise at least one muscle, ligament, tendon, cartilage, spinal disc, spinal foraminal space near the spinal nerve root, facet or spinal canal. Also by way of example, the inflammation may be associated with orthopedic or spine surgery or a combination thereof. By way of further example, the surgery may be arthroscopic surgery, an excision of a mass, hernia repair, spinal fusion, thoracic, cervical, or lumbar surgery, pelvic surgery or a combination thereof. In some embodiments, the active ingredient may provide longer duration of pain and/or inflammation relief for chronic diseases/conditions as discussed above with release of one or more drugs up to 6 months or 1 year (e.g., 90, 100, 135, 150, 180 days or longer).

In some embodiments, the at least one alpha adrenergic agonist or pharmaceutically acceptable salt thereof is encapsulated in a plurality of depots comprising microparticles, microspheres, microcapsules, and/or microfibers suspended in a gel.

In some embodiments, a method is provided of inhibiting pain and/or inflammation in a patient in need of such treatment, the method comprising delivering one or more biodegradable drug depots comprising a therapeutically effective amount of at least one alpha adrenergic agonist or pharmaceutically acceptable salt thereof to a target tissue site beneath the skin before, during or after surgery, wherein the drug depot releases an effective amount of at least one alpha adrenergic agonist or pharmaceutically acceptable salt thereof over a period of 3 days to 6 months.

In some embodiments, an implantable drug depot useful for preventing or treating pain and/or inflammation in a patient in need of such treatment is provided, the implantable drug depot comprising a therapeutically effective amount of at least one alpha adrenergic agonist or pharmaceutically acceptable salt thereof, the depot being implantable at a site beneath the skin to prevent or treat inflammation, wherein the drug depot releases an effective amount of at least one alpha adrenergic agonist or pharmaceutically acceptable salt thereof over a period of 33 days to 6 months.

In some embodiments, an implantable drug depot is provided, wherein the drug depot (i) comprises one or more immediate release layer(s) that releases a bolus dose of at least one alpha adrenergic agonist or pharmaceutically acceptable salt thereof at a site beneath the skin and (ii) one or more sustain release layer(s) that releases an effective amount of at least one alpha adrenergic agonist or pharmaceutically acceptable salt thereof over a period of 3 to 12 days or 5 to 10 days or 7 to 10 days or 3 days to 6 months. By way of example, in the drug depot, the one or more immediate release layer(s) may comprise poly (lactide-co-glycolide) (PLGA) and the one or more sustain release layer(s) may comprise polylactide (PLA).

Method of Making

In various embodiments, the drug depot comprising the active ingredients (e.g., alpha agonist) can be made by combining a biocompatible polymer and a therapeutically effective amount of the active ingredients or pharmaceutically acceptable salts thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients (e.g., alpha agonist), optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent (e.g., alpha agonist) under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic (e.g., clonidine) because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as active ingredients are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also be made by combining a biocompatible polymer and a therapeutically effective amount of at least one alpha adrenergic agonist or pharmaceutically acceptable salt thereof and forming the implantable drug depot from the combination.

Having now generally described the invention, the same may be more readily understood through the following reference to the following examples, which are provided by way of illustration and are not intended to limit the present invention unless specified.

EXAMPLES

The examples below show certain particularly advantageous results wherein the initial burst is not too large (i.e., not more than 7% of the load drug in the first five days) and the daily does is approximately 2.4 μg/day±0.5 μg/day for 135 days. See e.g., FIGS. 10 and 11; 14; and 19. The figures further demonstrate that drug loadings 5 wt. % to 8 wt. % provide advantageous results.

Figure 3:
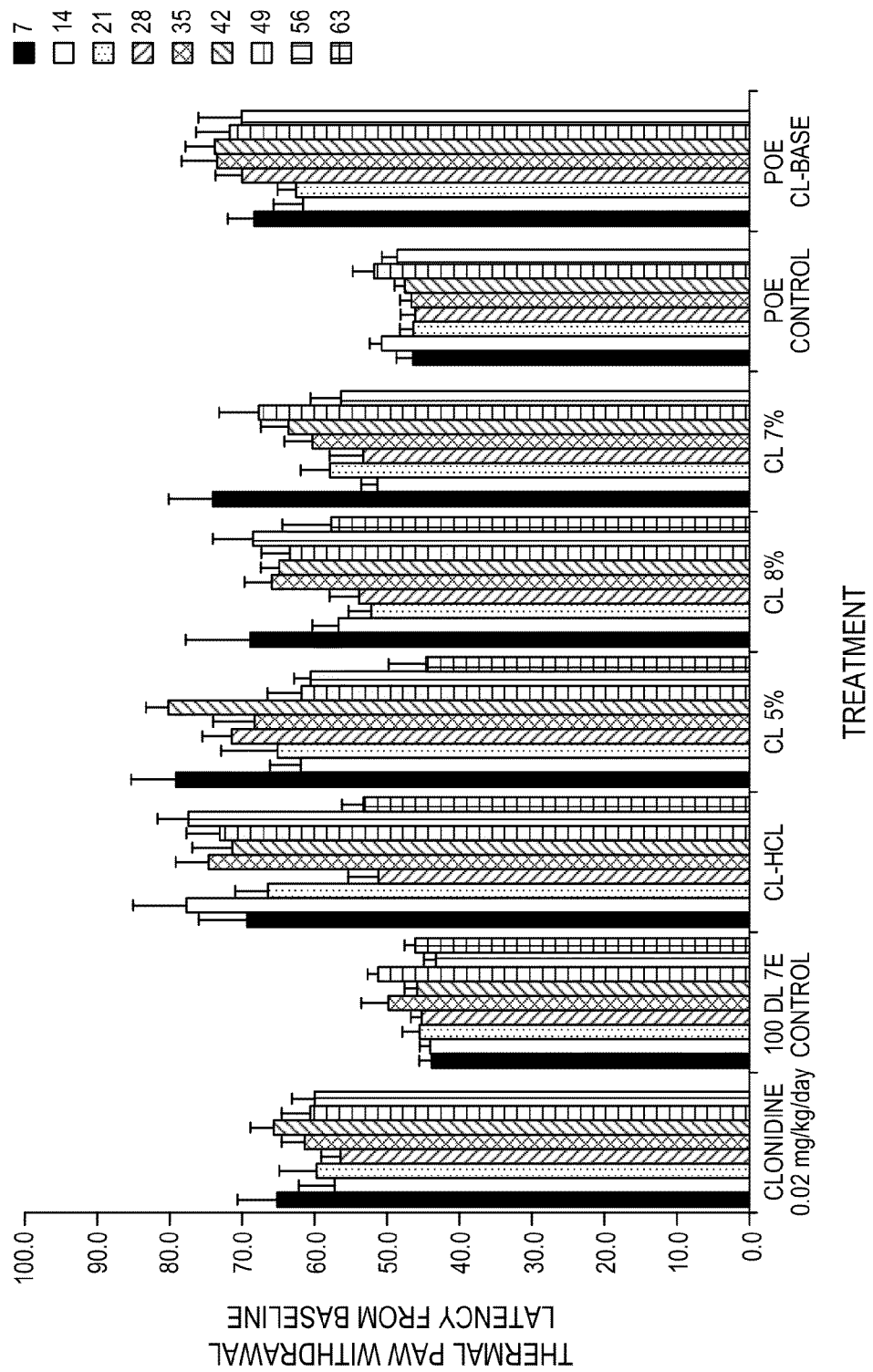
FIG. 3 is a graphic representation of the thermal paw withdrawal latency as a percentage from baseline for the following administrations using an alpha-2 adrenergic receptor agonist: clonidine 0.02 mg/kg/day subcutaneously, 100 DL 7E Control, 5% CL-HCL, CL 5%, CL 8%, 1 CL 7%, POE Control and POE CL-Base, at 7 days, 14 days, 21 days, 28 days, 35 days, 42 days, 49 days, 56 days and 63 days. CL-HCL refers to clonidine hydrochloride. "POE" refers to poly(orthoester). "CL-Base" refers to clonidine in its base form.
Figure 4:
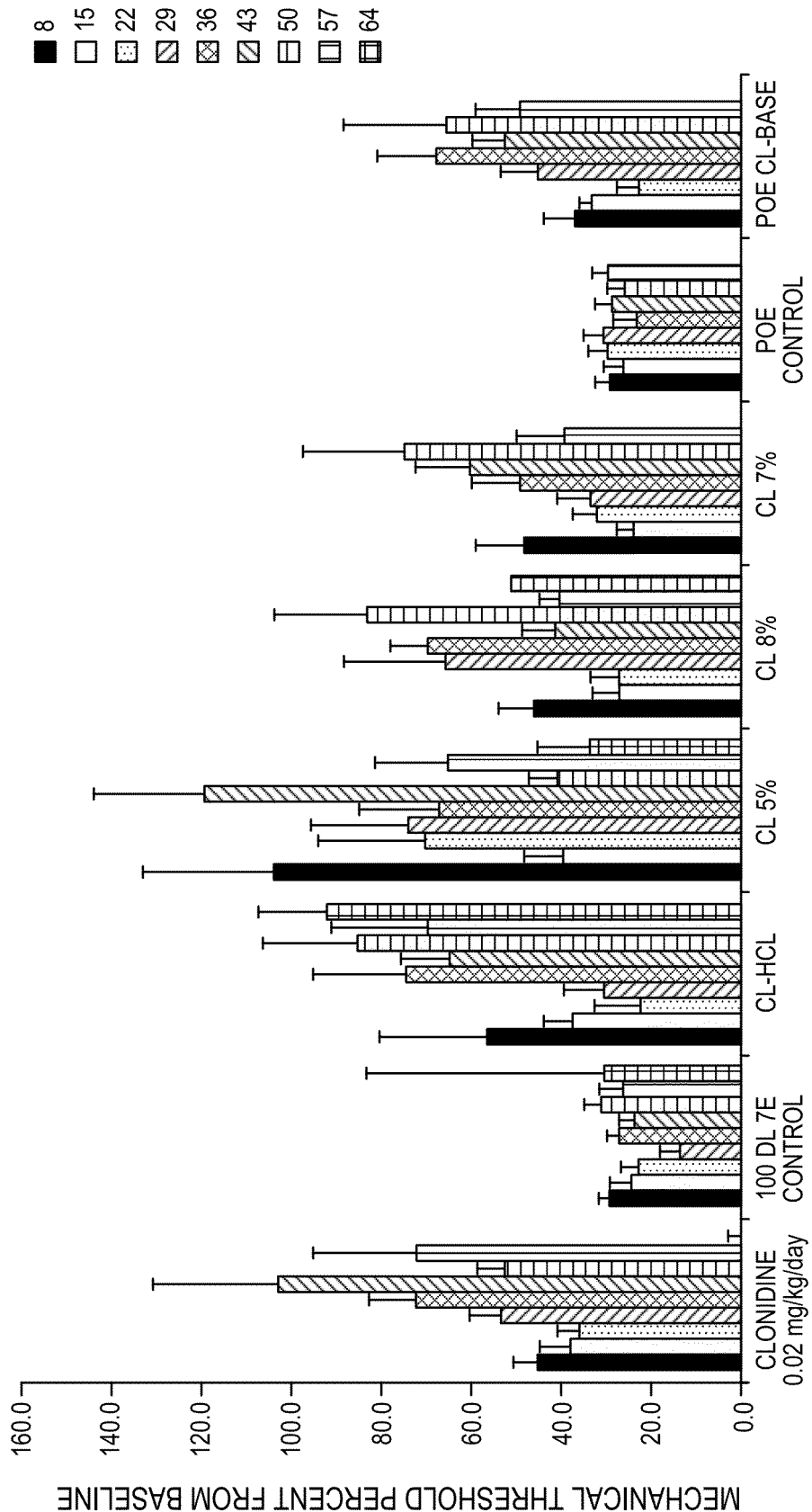
FIG. 4 is a graphic representation of the mechanical threshold as a percentage from baseline for the following administrations: clonidine 0.02 mg/kg/day subcutaneously, 100 DL 7E Control, 5% CL-HCL, CL 5%, CL 8%, CL 7%, POE Control and POE CL-Base, at 8 days, 15 days, 22 days, 29 days, 36 days, 43 days, 50 days, 57 days and 64 days.

A 2-month chronic constriction injury (CCI) model of neuropathic pain was used to evaluate different formulations of clonidine encapsulated in bioerodable polymers compared to clonidine given subcutaneously (SC). Different formulations as provided in Table 5 below were evaluated for reducing pain-associated behaviors: Thermal paw withdrawal latency was evaluated at baseline 7, 14, 21, 28, 35, 42, 49, 56 and 64 days post-operatively, while mechanical threshold was evaluated at 8, 15, 22, 29, 36, 43, 50, 57 and 64 days post-operatively. Bar graphs depicting the results of theses tests are shown in FIGS. 3-4.

The In-Vitro Elution Studies were carried out at 37° C. in phosphate-buffered saline (PBS, pH 7.4). Briefly, the rods (n=3) were weighed prior to immersion in 5 mL of PBS. At regular time intervals, the PBS was removed for analysis and replaced with 5 mL of fresh PBS. The PBS-elution buffer was analyzed for clonidine content using UV-Vis spectrometry.

Example 1

Formulation Testing

The inventors prepared a number of clonidine formulations in which they varied the polymer type, drug load, excipient (including some formulations in which there was no excipient), pellet size and processing. These formulations are described below in Table 1, Table 2 and Table 3. A number of tests were performed on these formulations, including in vitro release tests in which the number of micrograms released was measured, as well as the cumulative percentage release of clonidine. The results of these tests appear in FIGS. 7-34.

The In-Vitro Elution Studies were carried out at 37° C. in phosphate-buffered saline (PBS, pH 7.4). The rods (n=3) were weighed prior to immersion in 5 mL of PBS. At regular time intervals, the PBS was removed for analysis and replaced with 5 mL of fresh PBS. The PBS-elution buffer was analyzed for clonidine content using UV-Vis spectrometry.

TABLE 1

| Notebook ID | Polymer Type | Drug Load (Wt %) | Excipient | Pellet Size (L × Dia; mm) or Description | Processing |
|---|---|---|---|---|---|
| 13335-60-1 | 8515 DLG 7E | 10 | N/A | 0.75 × 0.75 | Melt extrusion, co-spray dried drug/polymer |
| 13335-60-2 | 8515 DLG 7E | 10 | N/A | 0.75 × 0.75 | Melt extrusion, spray dried drug |
| 13335-60-3 | 8515 DLG 7E | 10 | N/A | 0.75 × 0.75 | Melt extrusion, hand ground drug |
| 13335-60-4 | 8515 DLG 7E | 10 | N/A | 0.75 × 0.75 | Melt extrusion, hand ground drug, spray dried polymer |
| 13335-60-5 | 8515 DLG 7E | 10 | N/A | 0.75 × 0.75 | Melt extrusion w/ recycle loop, hand ground drug |
| 13335-65-1 | 8515 DLG 7E | 5 | N/A | 3.0 × 0.75 | Melt extrusion, spray dried drug |
| 13335-65-2 | 8515 DLG 7E | 10 | N/A | 1.5 × 0.75 | Melt extrusion, spray dried drug |
| 13335-65-3 | 8515 DLG 7E | 20 | N/A | 0.75 × 0.75 | Melt extrusion, spray dried drug |
| 13335-65-4 | 100 DL 7E | 5 | N/A | 3.0 × 0.75 | Melt extrusion, spray dried drug |
| 13335-65-5 | 100 DL 7E | 10 | N/A | 1.5 × 0.75 | Melt extrusion, spray dried drug |
| 13335-65-6 | 100 DL 7E | 20 | N/A | 0.75 × 0.75 | Melt extrusion, spray dried drug |
| 13335-97-1 | 8515 DLG 7E | 7.5 | N/A | 3.0 × 0.75 | Melt extrusion, spray dried drug |
| 13335-97-2 | 100 DL 7E | 5 | N/A | 3.0 × 0.75 | Melt extrusion, spray dried drug |
| 13335-97-3 | 8515 DLG 7E | 5 | 10% mPEG | 3.0 × 0.75 | Melt extrusion, spray dried drug |
| 13335-97-4 | 100 DL 7E | 5 | 10% mPEG | 3.0 × 0.75 | Melt extrusion, spray dried drug |
| 13699-1-1 | 100 DL 7E | 5 | N/A | 3.0 × 0.75 | Melt extrusion, spray dried drug |
| 13699-16-1 | 8515 DLG 7E | 10 | N/A | 1.5 × 0.75 | Melt extrusion, spray dried drug |
| 13699-16-2 | 9010 DLG 7E | 10 | N/A | 1.5 × 0.75 | Melt extrusion, spray dried drug |
| 13699-16-3 | 9010 DLG 7E | 5 | N/A | 3.0 × 0.75 | Melt extrusion, spray dried drug |
| 13699-16-4 | 8515 DLG 7E | 5 | 5% mPEG | 3.0 × 0.75 | Melt extrusion, spray dried drug |
| 13699-16-5 | 8515 DLG 7E | 5 | 2.5% mPEG | 3.0 × 0.75 | Melt extrusion, spray dried drug |
| 13699-20-1 | 8515 DLG 7E | 5 | 1% MgO | 3.0 × 0.75 | Melt extrusion, spray dried drug |
| 13699-20-4 | 8515 DLG 7E | 5 | N/A | 3.0 × 0.75 | Melt extrusion, spray dried drug |
| 13699-20-5 | 100 DL 7E | 5 | 10% 5050 DLG 6E | 3.0 × 0.75 | Melt extrusion, spray dried drug |
| 13699-20-6 | 100 DL 7E | 5 | 10% 5050 DLG 1A | 3.0 × 0.75 | Melt extrusion, spray dried drug |
| 13699-20-7 | 8515 DLG Purac | 10 | N/A | 1.5 × 0.75 | Melt extrusion, spray dried drug |
| 13699-20-8 | 8515 DLG 7E | 5 | N/A | 3.0 × 0.75 | Melt extrusion 2X, spray dried drug |
| 13699-28-1 | 8515 DLG Purac | 7.5 | N/A | 3.0 × 0.75 | Melt extrusion, spray dried drug |
| 13699-28-2 | 8516 DLG Purac | 12.5 | N/A | 2.0 × 0.75 | Melt extrusion, spray dried drug |
| 13699-28-3 | 100 DL 7E | 5 | N/A | 3.0 × 0.75 | Melt extrusion, spray dried drug |
| 13699-31-1 | 8515 DLG 7E | 10 | N/A | N/A | heat press, spray dried drug |
| 13699-31-2 | 8515 DLG 7E | 10 | N/A | N/A | heat press, spray dried drug |
| 13699-31-3 | 8515 DLG 7E | 10 | N/A | N/A | heat press, spray dried drug |
| 13699-31-4 | 8515 DLG 7E | 10 | N/A | N/A | Melt extrusion, spray dried drug |
| 12702-13-4-a | 1,6-Hexanediol/tCHDM | 10 | N/A | 3 × 3 | Melt extrusion |

TABLE 1-continued

| Notebook ID | Polymer Type | Drug Load (Wt %) | Excipient | Pellet Size (L × Dia; mm) or Description | Processing |
|---|---|---|---|---|---|
| 12702-13-4-b | 75/25 PLGA | 10 | N/A | 3 × 3 | Melt extrusion |
| 12702-68-12 | 75/25 PLGA | 5 | mPEG | 1 × 1 | Melt extrusion |
| 12702-68-13 | 75/25 PLGA | 5 | TBO-Ac | 1 × 1 | Melt extrusion |
| 12702-72-1 | 75/25 PLGA | 5 | mPEG | 1 × 1 | Melt extrusion |
| 12702-80-7 | 75/25 PLGA | 10 | mPEG | 0.75 × 0.75 | Melt extrusion |
| 12702-80-8 | 75/25 PLGA | 15 | mPEG | 0.75 × 0.75 | Melt extrusion |
| 13395-3-1 | 85/15 PLGA | 10 | mPEG | 0.75 × 0.75 | Melt extrusion |
| 13395-3-2 | 85/15 PLGA | 15 | mPEG | 0.75 × 0.75 | Melt extrusion |
| 13395-3-3 | 85/15 PLGA | 5 | mPEG | 0.75 × 0.75 | Melt extrusion |
| 13395-15 | 85/15 PLGA | 15 | mPEG | 0.75 × 0.75 | Melt extrusion |
| 13395-20-1 | 85/15 PLGA | 5 | Span-85 | 0.75 × 0.75 | Melt extrusion |
| 13395-20-2 | 85/15 PLGA | S | Pluronic-F127 | 0.75 × 0.75 | Melt extrusion |
| 13395-20-3 | 85/15 PLGA | 5 | N/A | 0.75 × 0.75 | Melt extrusion |
| 13395-21-1 | D,L-PLA | 5 | mPEG | 0.75 × 0.75 | Melt extrusion |
| 13395-21-2 | 85/15 PLGA | 5 | TBO-Ac | 0.75 × 0.75 | Melt extrusion |
| 13395-24-1 | 85/15 PLGA | 5 | Span-65 | 0.75 × 0.75 | Melt extrusion |
| 13395-27-1 | 85/15 PLGA | 10 | N/A | 0.75 × 0.75 | Melt extrusion |
| 13395-27-2 | 85/15 PLGA | 15 | N/A | 0.75 × 0.75 | Melt extrusion |
| 13395-27-3 | 85/15 PLGA | 10 | Span-65 | 0.75 × 0.75 | Melt extrusion |
| 13395-27-4 | 85/15 PLGA | 10 | TBO-Ac | 0.75 × 0.75 | Melt extrusion |
| 13395-27-5 | 85/15 PLGA | 10 | Pluronic F127 | 0.75 × 0.75 | Melt extrusion |
| 13395-34-2 | D,L-PLA | 10 | N/A | 0.75 × 0.75 | Melt extrusion |
| 13395-34-3 | D,L-PLA | 10 | TBO-Ac | 0.75 × 0.75 | Melt extrusion |
| 13395-34-4 | D,L-PLA | 10 | mPEG | 0.75 × 0.75 | Melt extrusion |
| 13395-42-1 | DL-PLA/PCL | 10 | N/A | 0.75 × 0.75 | Melt extrusion |
| 13395-42-2 | DL-PLA/PCL | 15 | N/A | 0.75 × 0.75 | Melt extrusion |

TABLE 2

| Notebook ID | Polymer Type | Drug Load (Wt %) | Excipient | Pellet Size (L × Dia; mm) or Description | Processing |
|---|---|---|---|---|---|
| 13335-73-1 | POE 58 | 10 | N/A | 1.5 × 0.75 | Melt extrusion |
| 13335-73-2 | POE 58 | 20 | N/A | 0.75 × 0.75 | Melt extrusion |
| 13335-73-3 | POE 60 | 10 | N/A | 1.5 × 0.75 | Melt extrusion |
| 13335-73-4 | POE 60 | 20 | N/A | 0.75 × 0.75 | Melt extrusion |
| 13699-1-2 | POE 58 | 10 | N/A | 4-1.5 × 0.75 | Melt extrusion |
| 13699-1-3 | POE 58 | 20 | N/A | 1-0.75 × 0.75 | Melt extrusion |
| 12702-23 | tCHDM (100) | 25 | N/A | Microspheres | Double emulsion |
| 12702-26 | tCHDM/DET (70/30) | 4.2 | N/A | Microspheres | Double emulsion |
| 12702-54 | 75/25 PLGA | 20 | N/A | Microspheres | Double emulsion |
| 12702-68-9 | 75/25 PLGA | 5 | mPEG | 3 × 3 | Melt extrusion |
| 12702-68-10 | 75/25 PLGA | 5 | TBO-Ac | 3 × 3 | Melt extrusion |
| 12702-87 | 75/25 PLGA | 15 | mPEG |  | Mixer-Molder |
| 12702-90 | 85/15 PLGA | 17 | N/A |  | Mixer-Molder |
| 12702-78-1 | Polyketal (12833-14-1) | 7 | N/A | 2 × 3 | Melt extrusion |
| 13395-14 | 50/50 PLGA (2A) | 10 | mPEG | N/A | Melt extrusion |
| 13395-17-1 | POE (13166-75) | 5 | N/A | 1.5 × 1.5 | Melt extrusion |
| 13395-17-2 | POE (13166-77) | 5 | N/A | 1.5 × 1.5 | Melt extrusion |
| 13395-47-1 | DL-PCL | 10 | N/A | 1.3 × 1.3 | Melt extrusion |
| 13395-50 | DL-PCL | 10 | N/A | 1.3 × 1.3 | Melt extrusion; w/ solvent prep |
| 13395-51 | D,L-PLA | 10 | mPEG | N/A | Melt extrusion |

TABLE 3

| Notebook ID | Polymer Type | Drug Load (Wt %) | Processing |
|---|---|---|---|
| 00178-23 | 100 DL 5E | 8.1 | Grind drug with mortar/pestile, blend with spatula, coarsely mixed |
| 00178-15 | 100 DL 7E | 7.2 | Grind drug with mortar/pestile, blend with spatula, coarsely mixed |

TABLE 3-continued

| Notebook ID | Polymer Type | Drug Load (Wt %) | Processing |
|---|---|---|---|
| 00178-35 | 100 DL 5E | 5 | Grind drug with mortar/pestile, blend with spatula, coarsely mixed |
| 00178-16 | 100 DL 7E | 10.2 | Grind drug with mortar/pestile, blend with spatula, coarsely mixed |
| 00178-21 | 8515 DL 7E | 7.3 | Grind drug with mortar/pestile, blend with spatula, coarsely mixed |
| 00178-36 | 100 DL 7E | 5 | Grind drug with mortar/pestile, blend with spatula, coarsely mixed |
| 00178-44 | 100 DL 7E | 5.1 | Dissolved in glacial acetic acid and freeze dried |
| 00178-45 | 100 DL 7E | 4.5 | Drug and polymer blended by mortar/pestile, finely mixed, under N2 |
| 00178-63 | 100 DL 7E | 9.4 | Drug and polymer blended by mortar/pestle, finely mixed |
| 00178-08 | 100 DL 7E | 21.4 | Blend with spatula, no reduction in drug particle size |
| 00178-11 | 100 DL 7E | 7.9 | Blend with spatula, no reduction in drug particle size |
| 00178-12 | 100 DL 7E | 11.7 | Blend with spatula, no reduction in drug particle size |
| 00178-22 | 8515 DL 7E | 83.3 | Grind drug with mortar/pestile, blend with spatula, coarsely mixed |
| 00178-24 | 100 DL 5E | 10.1 | Grind drug with mortar/pestile, blend with spatula, coarsely mixed |
| tab 11 | 100 DL 5E | 5 | |
| tab 11 | 100 DL 7E | 5 | |
| tab 11 | 100 DL 5E | 5 | EtOAc coating |
| tab 11 | 100 DL 7E | 5 | EtOAc coating |
| tab 11 | 100 DL 7E | 5 | Glacial HoAc dissolution |
| tab 11 | 100 DL 7E | 5 | prepared in N2 environment |
| 00178-72 | 100 DL 7E | 4.5 | Double Extrusion (20% diluted to 5%) |
| 00178-73 | 100 DL 7E | 8.7 | Double Extrusion (20% diluted to 10%) |
| 00178-74 | 100 DLG 7E | 7.3 | API mixed with polymer using mortar/pestle |
| 00178-71 | 6535 DLG 7E | 5.3 | API mixed with polymer using mortar/pestle |
| 00178-75 | 6535 DLG 7E | 5.3 | API mixed with polymer using mortar/pestle |
| 00178-76-R1 | 100 DL 7E core with 100DL coating | 7.76 | coaxial extrusion, 4 different coating thicknesses |
| 00178-76-R2 | 101 DL 7E core with 100DL coating | 6.92 | coaxial extrusion, 4 different coating thicknesses |
| 00178-76-R3 | 102 DL 7E core with 100DL coating | 6.76 | coaxial extrusion, 4 different coating thicknesses |
| 00178-76-R4 | 103 DL 7E core with 100DL coating | 8 | coaxial extrusion, 4 different coating thicknesses |
| 00178-79-R1 | 100 DL 5E core with 100DL 5E coating | 15 | coaxial extrusion, thin coat |
| 00178-79-R2 | 100 DL 5E core with 100DL 5E coating | 15 | coaxial extrusion, thick coat |
| 00178-80-R1 | 100 DL 5E core with 100DL 5E coating | 7.54 | coaxial extrusion, different coating thicknesses |
| 00178-80-R2 | 100 DL 5E core with 100DL 5E coating | 8.9 | coaxial extrusion, different coating thicknesses |
| 00178-80-R3 | 100 DL 5E core with 100DL 5E coating | 9.39 | coaxial extrusion, different coating thicknesses |
| 00178-77 | 100 DL 5E | 5 | repeat of 178-35 (0.8 MM & 1.0 mm diam) |
| 00178-78 | 100 DL 5E | 5 | repeat of 178-35 (0.8 MM & 1.0 mm diam) |
| 00178-81 | 100 DL 5E | 7.2 | repeat of 178-23 |
| 00178-23B | | | EtOAc coating |
| 00178-23C | | | Polymer soln coating |

The codes within the table for the polymer are explained as follows. The first number or numbers refer to monomer mole percentage ratio of DL-lactide (e.g., polylactide) to glycolide (e.g., poly-glycolide). The letter code that follows the first number refers to the polymer(s) and is the polymer identifier. The second number, which follows the letter code for the polymer, is the target IV designator and is 10 times the midpoint of a range in dl/g. The meanings of certain IV designators are reflected in Table 4.

TABLE 4

| IV Target Designator | IV Range |
|---|---|
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |

The final letter within the code of the polymer is the end group designator. For examples "E" refers to an ester end group, while "A" refers to an acid end group.

By way of example, 100 DL 7E is a polymer that has an inherent viscosity of 0.60-0.80 dL/g. It contains 100% poly (DL-lactide) that has ester end groups. It is available from Lakeshore Biomaterials, Birmingham, Ala.

Example 2

The inventors evaluated the efficacy of a five Month Clonidine/Polymer Drug Depot in the Rat Chronic Constriction Injury Model. The animal model was the Bennett Model (Wistar rat). The purpose: To determine whether a five month polymer clonidine-eluting depot can improve pain associated behavioral responses in a rat model of neuropathic pain.

Experimental Design: Four loose chromic gut ligatures, 1 mm apart, were tied around the common sciatic nerve at mid-thigh. Each animal received treatment of test or control article-according to the dosing described in Table 5.

TABLE 5

| Group Number | Treatment | Dose | Comments |
|---|---|---|---|
| 1 | Clonidine | 0.02 mg/kg SC | Clonidine control |
| 2 | 100 DL 7E | 0% | 4 pellets (3 mm × 0.7 mm) |
| 3 | 100 DL 7E | 5% | Clonidine HCl; 4 pellets (3 mm × 0.7 mm) |
| 4 | 100 DL 5E | 5% | 3 pellets (3 mm × 0.7 mm) |
| 5 | 100 DL 5E | 7% | 3 pellets (3 mm × 0.7 mm) |
| 6 | 100 DL 7E | 7% | 3 pellets (3 mm × 0.7 mm) |
| 7 | POE | 0% | 5 pellets (1.5 mm × 0.7 mm) |
| 8 | POE | 10 and 20% | clonidine-base; 5 pellets (1 20% @ 0.7 mm$^{2;}$ 4 10% @ 1.5 mm × 0.7 mm) |

The inventors have conducted the present study for a period of 64 days and have employed the following two tests: (1) the Hargreaves test; and (2) the von Frey test. The Hargreaves Tests of Thermal Hyperalgesia were conducted on days 7, 14, 21, 28, 35, 42, 49, 56 and 63. The von Frey monofilament test of mechanical allodynia (performed the day following Thermal testing) were conducted on days-8, 15, 22, 29, 36, 43, 50, 57 and 64. The results of these tests are summarized in FIGS. 3 and 4 and show the efficacy of clonidine of the recited time periods. These results are summarized in FIGS. 3 and 4.

The pain behavioral response (measured as a percentage of baseline) for thermal hyperalgesia (FIG. 3) indicates that clonidine delivered subcutaneously at 0.02 mg/kg/day consistently reduced the behavioral response when compared to either unloaded polymer depots (100 DL 7W Control or POE Control) (58% vs. 45%). All five clonidine-loaded polymer depots were able to reduce pain behavioral responses when compared to unloaded depot; although, each formulation experienced a drop in efficacy at some point after the initial burst of drug at implantation. The pain behavioral response (measured as a percentage of baseline) for mechanical allodynia indicates that clonidine delivered subcutaneously at 0.02 mg/kg/day reduced the behavioral response when compared to either unloaded polymer depots (100 DL 7W Control or POE Control).

Example 3

Clonidine Drug Depot Release Profiles

Figure 5:
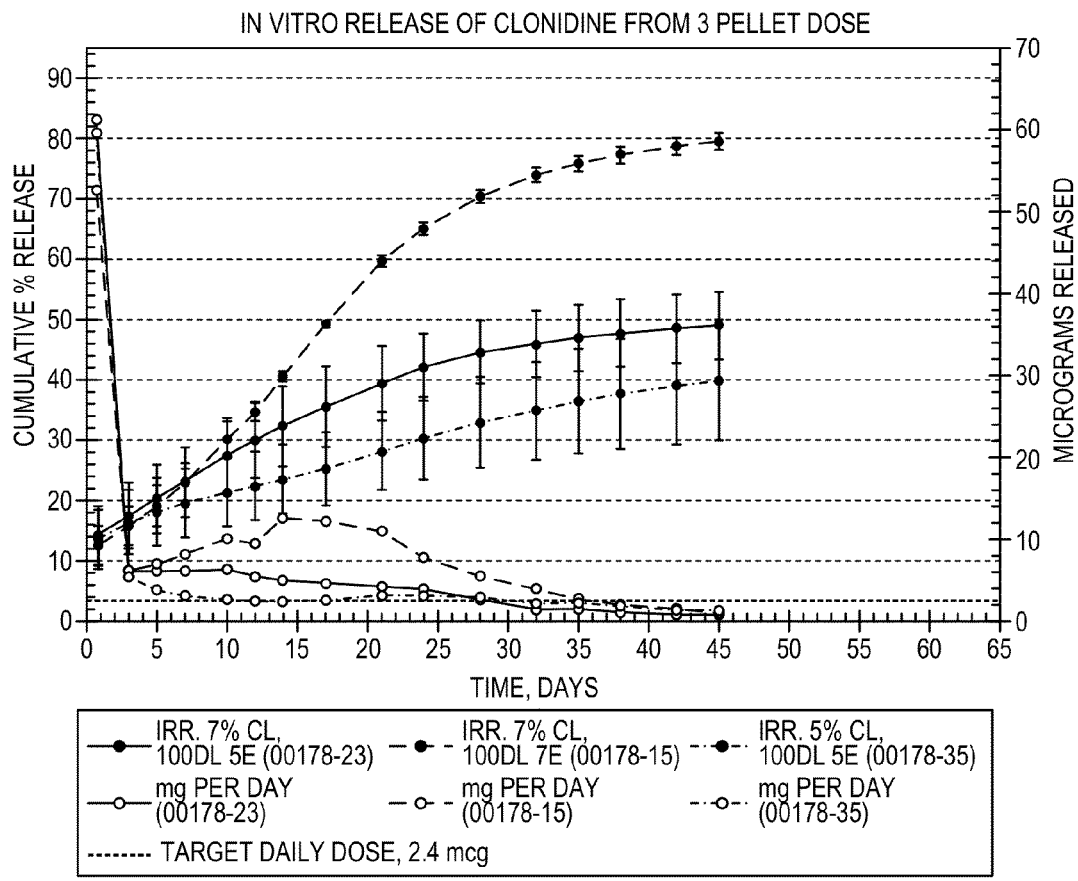
FIG. 5 is a graphic representation of an in vitro release of clonidine from three pellet doses as measured by percentage release and micrograms released.

FIG. 5 is a graphic representation of an in vitro release of clonidine from three pellet doses as measured by percentage release and micrograms released (Table 2). Some formulations released 80% of the clonidine for 45 days. The two, three, or four pellet doses mimics the doses that would be implanted in a human. All the formulations had an initial burst effect within the first two days, where the drug depot had a 10% to 80% cumulative release. In general, formulations with the higher drug loads had a faster release profile.

Figure 6:
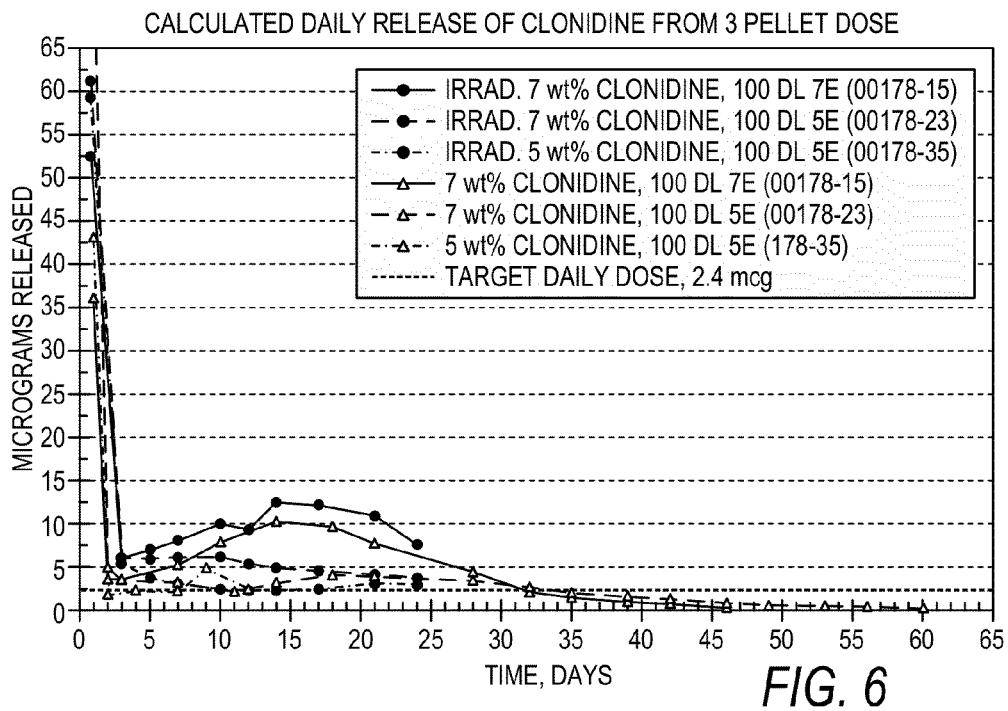
FIG. 6 is a graphic representation of the calculated daily release of clonidine from three pellet doses as measured by micrograms released.

FIG. 6 is a graphic representation of the calculated daily release of clonidine from three pellet doses as measured by micrograms released (Table 3). Some formulations released the clonidine over 60 days. The target daily dose was 2.4 mg/day. All the formulations had an initial burst effect within the first two days, where the drug depot released a bolus dose of about 35 to 65 mcg. In general, formulations with the higher drug loads had a faster release profile.

Figure 7:
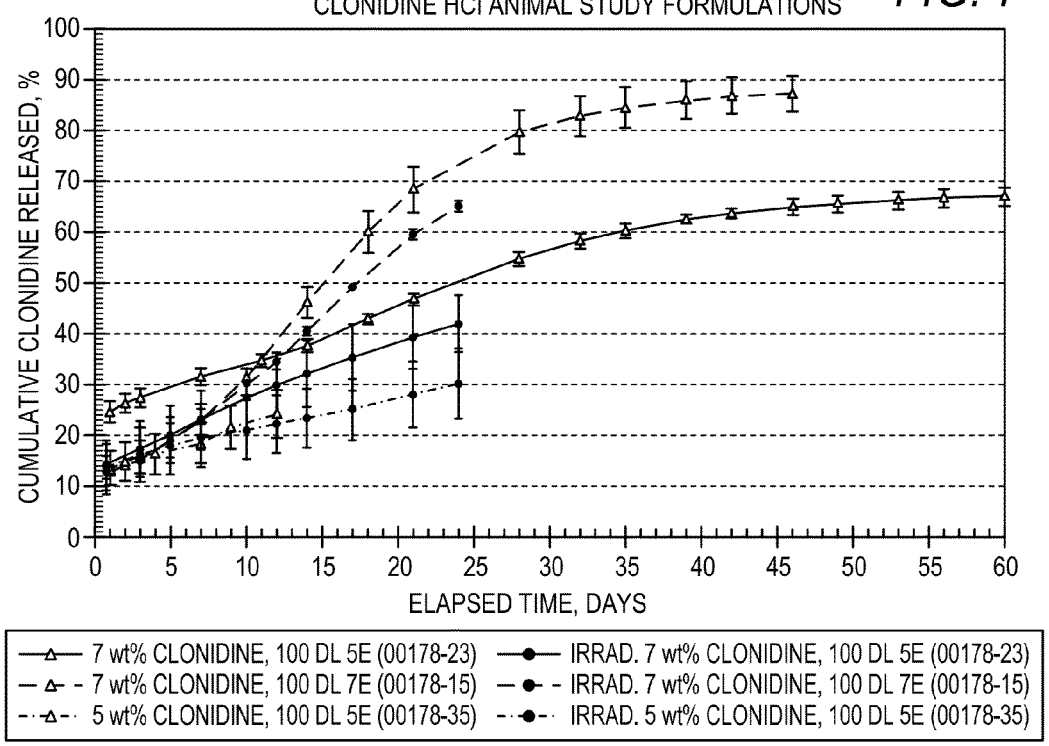
FIG. 7 is a graphic representation of clonidine HCl animal study formulations as measured by the cumulative clonidine released percentage.

FIG. 7 is a graphic representation of clonidine HCl animal study formulations as measured by the cumulative clonidine released percentage (Table 3). Some formulations released at least 60% of the clonidine for 60 days. In general, formulations with the higher drug loads had a longer release profile over 45 to 60 days.

Figure 8:
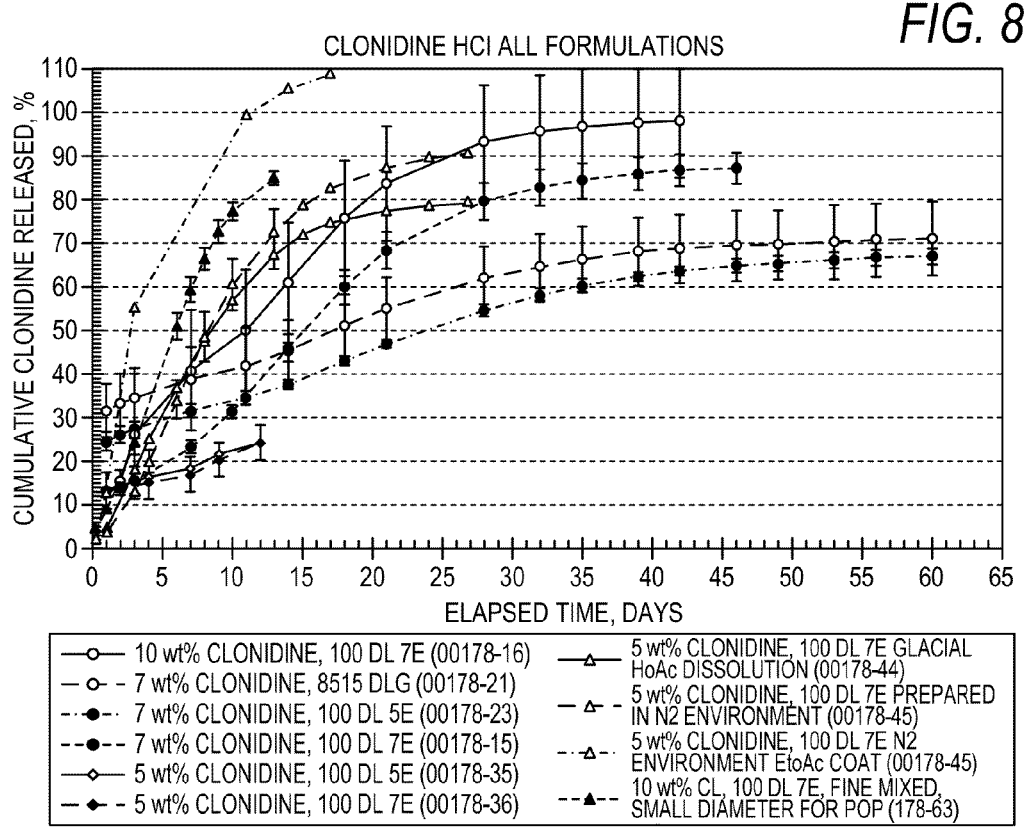
FIG. 8 is a graphic representation of clonidine HCl release for various formulations as measured by the cumulative clonidine released percentage.

FIG. 8 is a graphic representation of clonidine HCl release for various formulations (Table 3) as measured by the cumulative clonidine released percentage. Some formulations released at least 70% of the clonidine for 60 days. In general, formulations with the higher drug loads had a longer release profile over 60 days.

Figure 9:
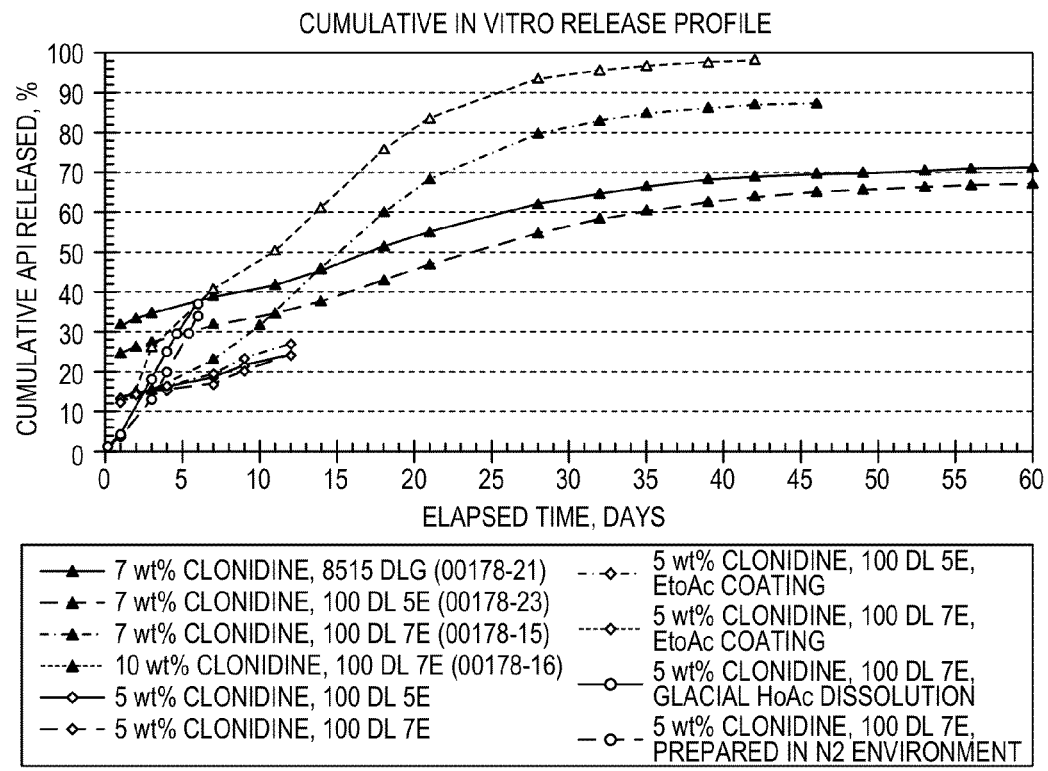
FIG. 9 is a graphic representation of the cumulative in vitro release profile for certain clonidine formulations.

FIG. 9 is a graphic representation of the cumulative in vitro release profile for certain clonidine formulations (Table 3). Some formulations released at least 60% of the clonidine for 60 days.

Figure 10:
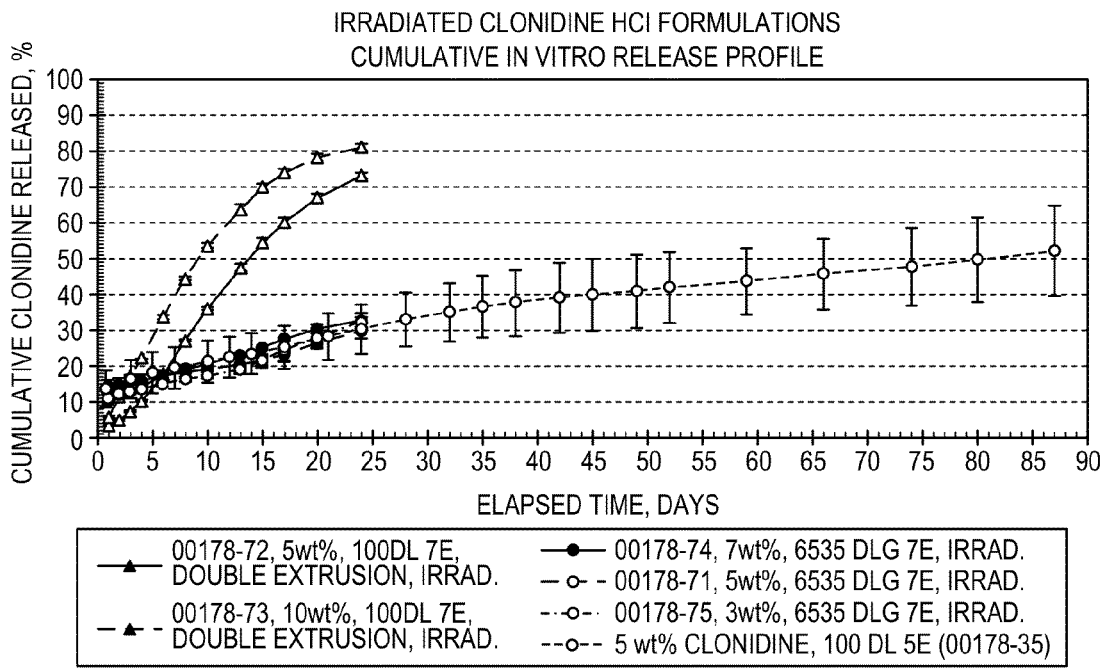
FIG. 10 is a graphic representation of the cumulative release profiles for certain irradiated clonidine HCl formulations.

FIG. 10 is a graphic representation of the cumulative release profiles for certain irradiated clonidine HCl formulations (Table 3). Some formulations released at least 50% of the clonidine for over 80 days.

Figure 11:
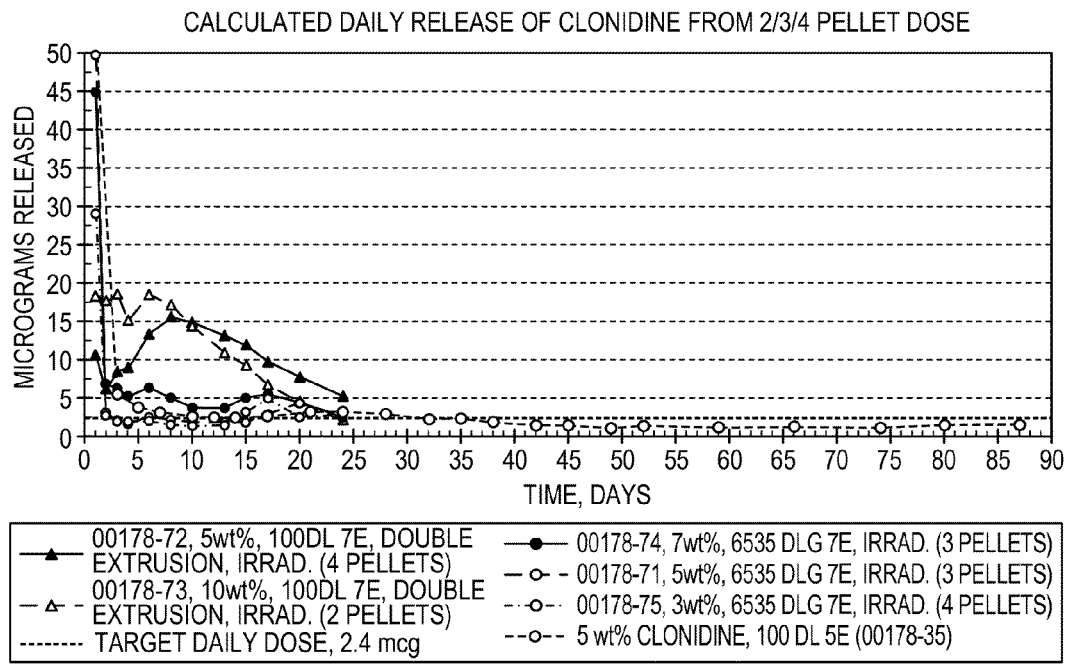
FIG. 11 is a graphic representation of certain calculated daily release measurements of clonidine from 2/3/4 pellets doses.

FIG. 11 is a graphic representation of certain calculated daily release measurements of clonidine from 2/3/4 pellets doses (these approximate human doses). Some formulations (Table 3) released clonidine for 85 days.

Figure 12:
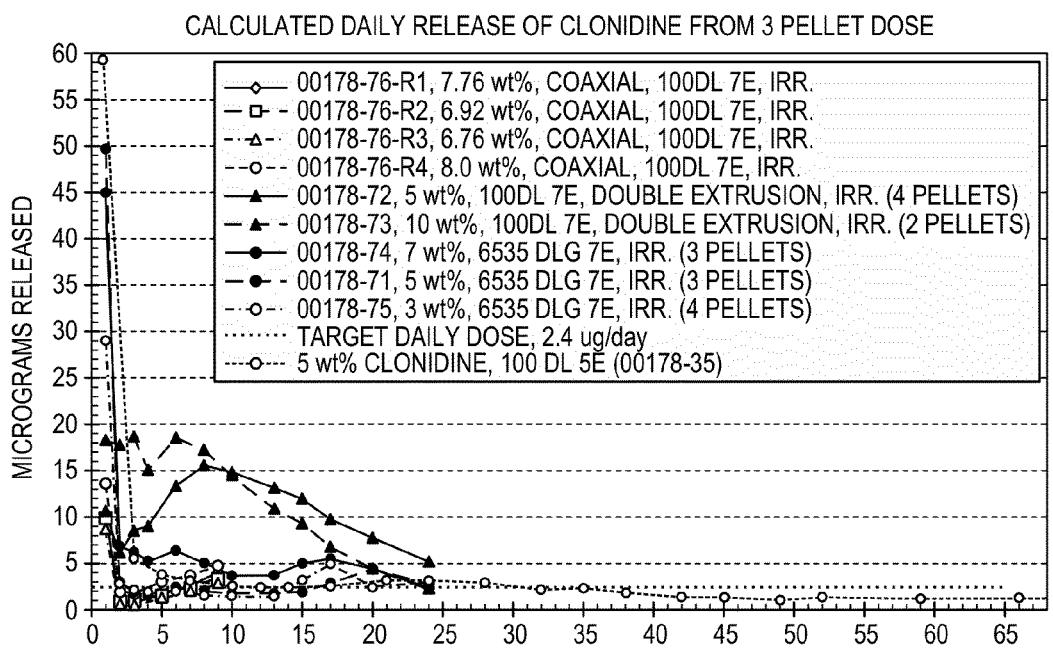
FIG. 12 is a graphic representation of the calculated daily release of clonidine from certain three pellet doses.

FIG. 12 is a graphic representation of the calculated daily release of clonidine from certain three pellet doses (Table 3). Some formulations released clonidine for over 65 days.

Figure 13:
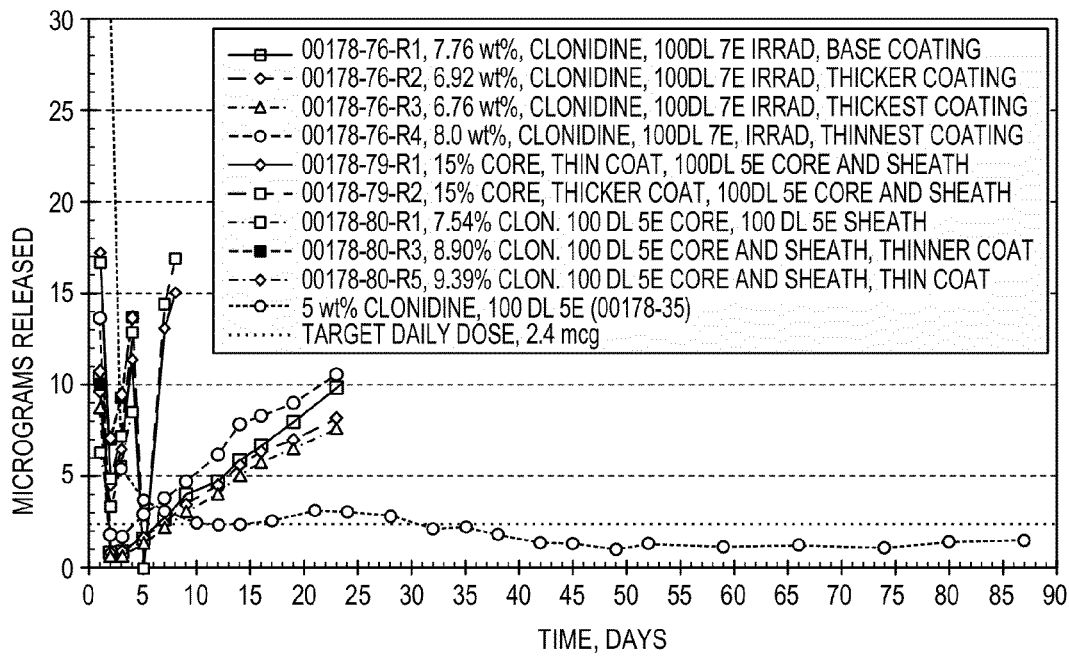
FIG. 13 is a graphic representation of the calculated daily release of clonidine from certain 2/3 pellet dose coaxial formulations.

FIG. 13 is a graphic representation of the calculated daily release of clonidine from certain 2/3 pellet dose coaxial formulations (Table 3). Some formulations released clonidine for over 85 days.

Figure 14:
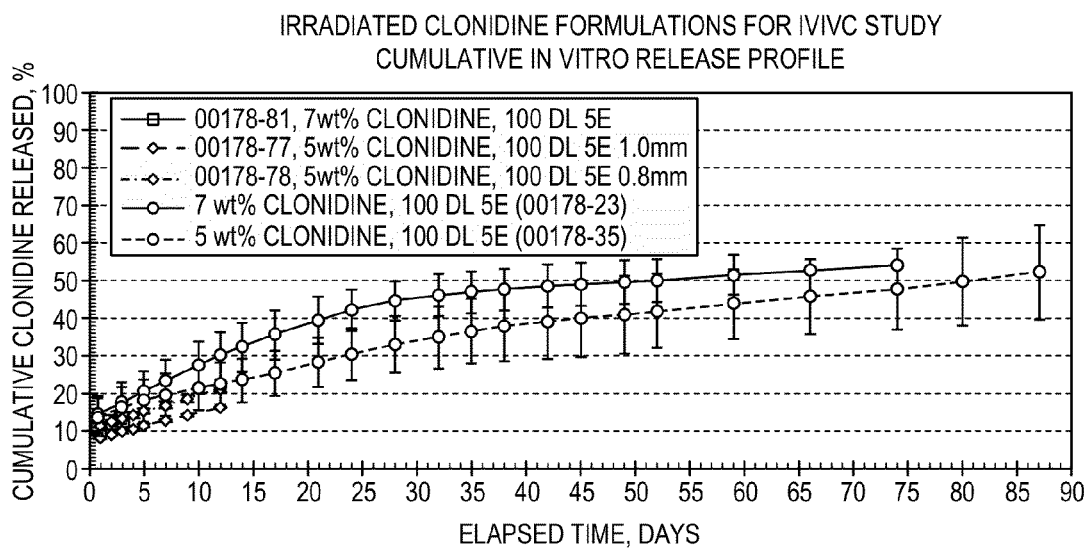
FIG. 14 is a graphic representation of the cumulative in vitro release profile for certain irradiated clonidine formulations.

FIG. 14 is a graphic representation of the cumulative in vitro release profile for certain irradiated clonidine formulations (Table 3). Some formulations released about 50% of the clonidine for over 85 days.

Figure 15:
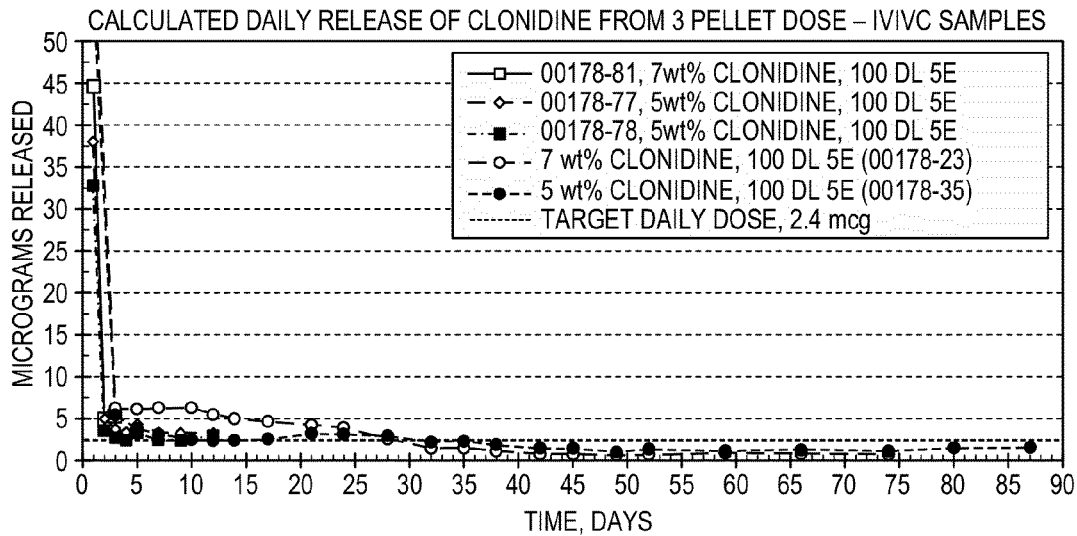
FIG. 15 is a graphic representation of the calculated daily release of clonidine for certain three pellet dose formulations.

FIG. 15 is a graphic representation of the calculated daily release of clonidine for certain three pellet dose formulations (Table 3). Some formulations released clonidine for over 85 days.

Figure 16:
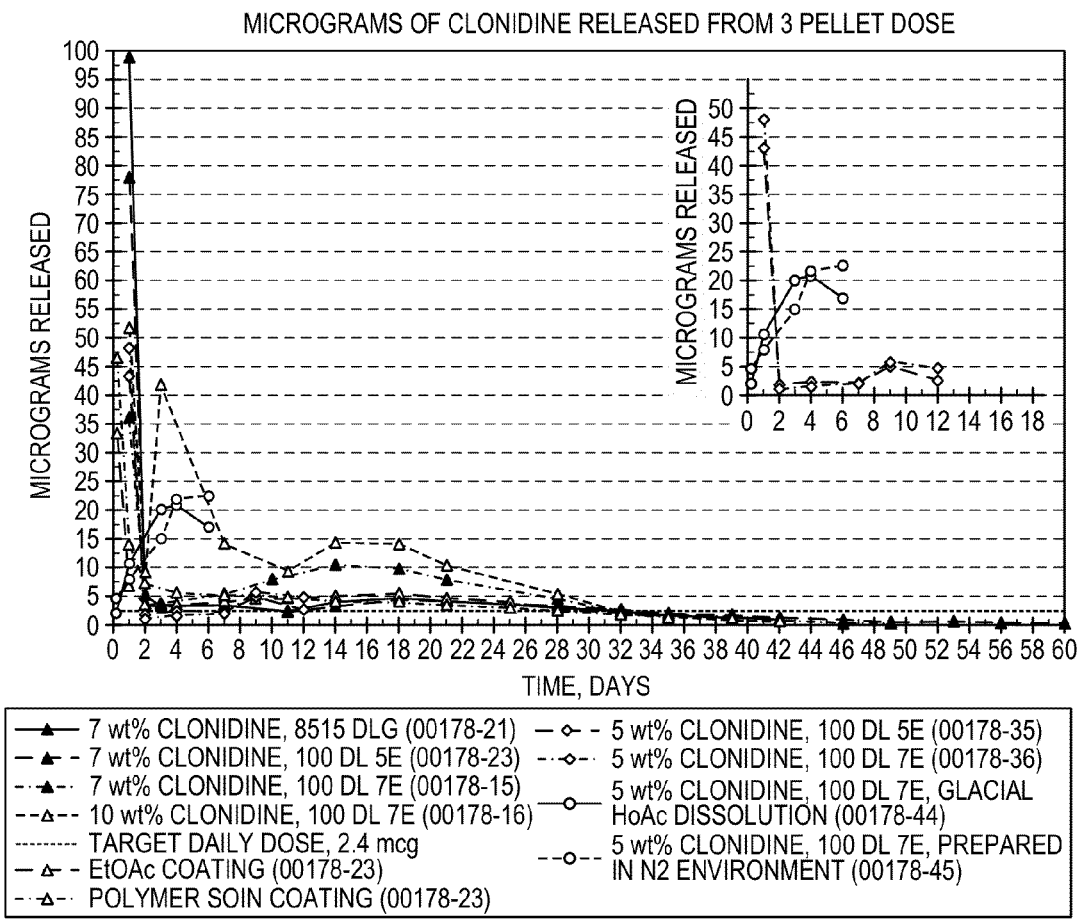
FIG. 16 is a graphic representation of the micrograms of clonidine released for certain three pellet dose formulations.

FIG. 16 is a graphic representation of the micrograms of clonidine released for certain three pellet dose formulations (Table 3). Some formulations had an initial burst effect for about 2 days, then a continuous daily release for over 60 days.

Figure 17:
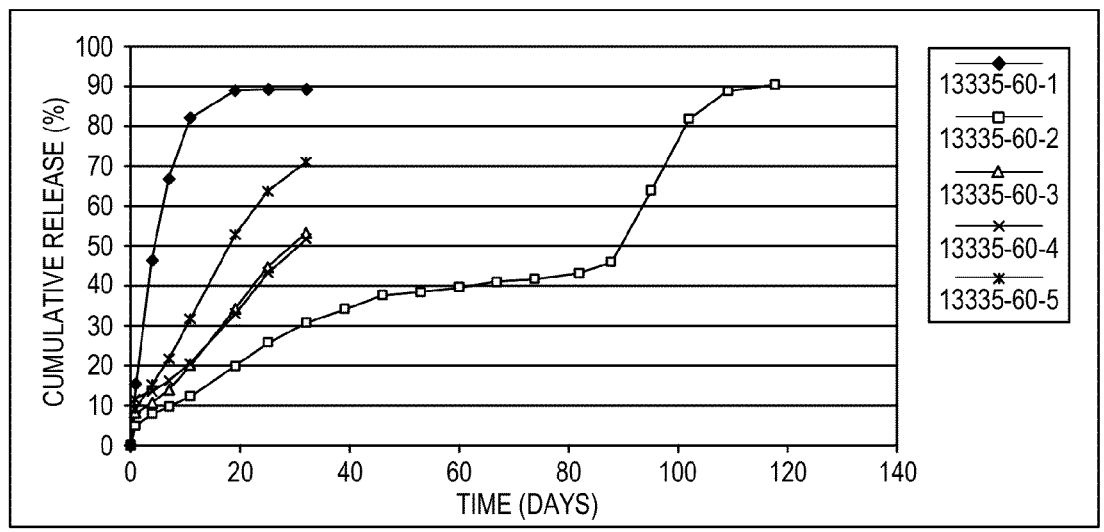
FIG. 17 is a graphic representation of the cumulative release percentage of clonidine for certain formulations.

FIG. 17 is a graphic representation of the cumulative release percentage of clonidine for certain formulations produced as indicated in Table 1. The formulation containing 10 wt % clonidine drug load and the polymer 8515 DLG 7E had about 90 cumulative release % of drug released from the depot as long as 120 days, which is suitable for many chronic conditions of pain and/or inflammation.

Figure 18:
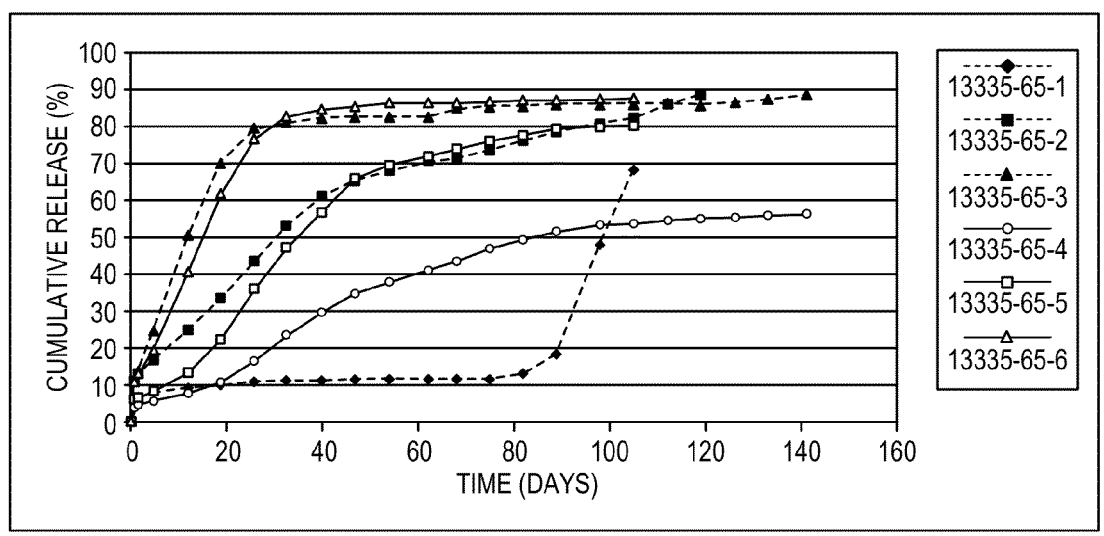
FIG. 18 is a graphic representation of the cumulative release percentage of clonidine for certain formulations.

FIG. 18 is a graphic representation of the cumulative release percentage of clonidine for certain formulations produced as indicated in Table 1. The formulation containing 20 wt % clonidine drug load and the polymer 8515 DLG 7E had about 90 cumulative release % of drug released from the depot as long as 140 days, which is suitable for many chronic conditions of pain and/or inflammation.

Figure 19:
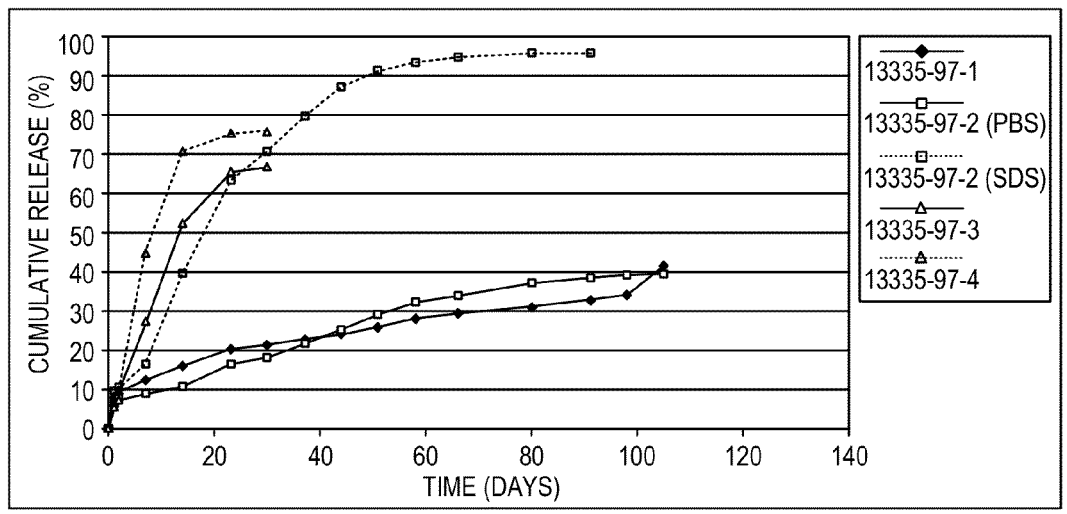
FIG. 19 is a graphic representation of the cumulative release percentage of clonidine for certain formulations.

FIG. 19 is a graphic representation of the cumulative release percentage of clonidine for certain formulations (Table 1). Some formulations released about 95% of the clonidine over 110 days.

Figure 20:
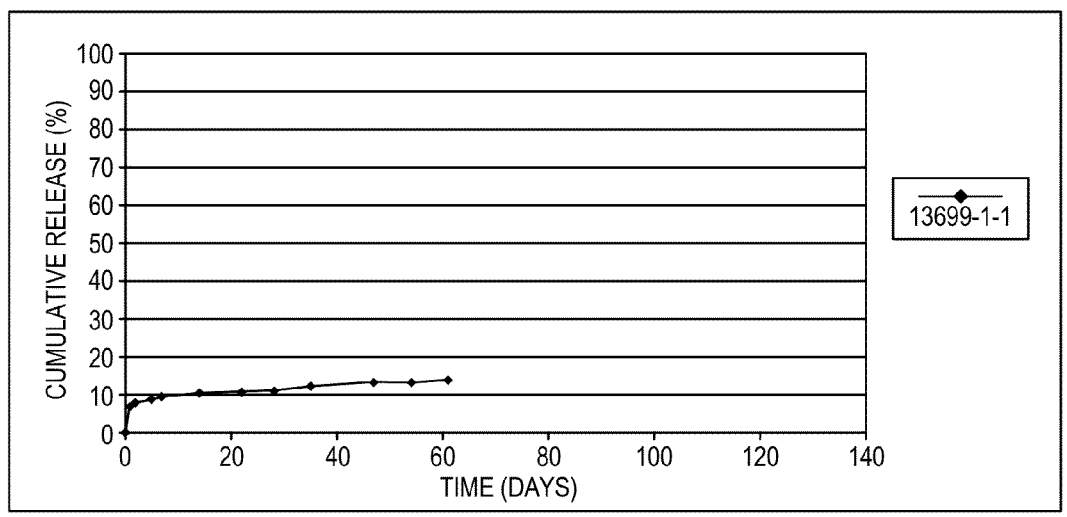
FIG. 20 is a graphic representation of the cumulative release percentage of clonidine for one formulation.

FIG. 20 is a graphic representation of the cumulative release percentage of clonidine for one formulation (Table 1) over 60 days. The release was relatively continuous.

Figure 21:
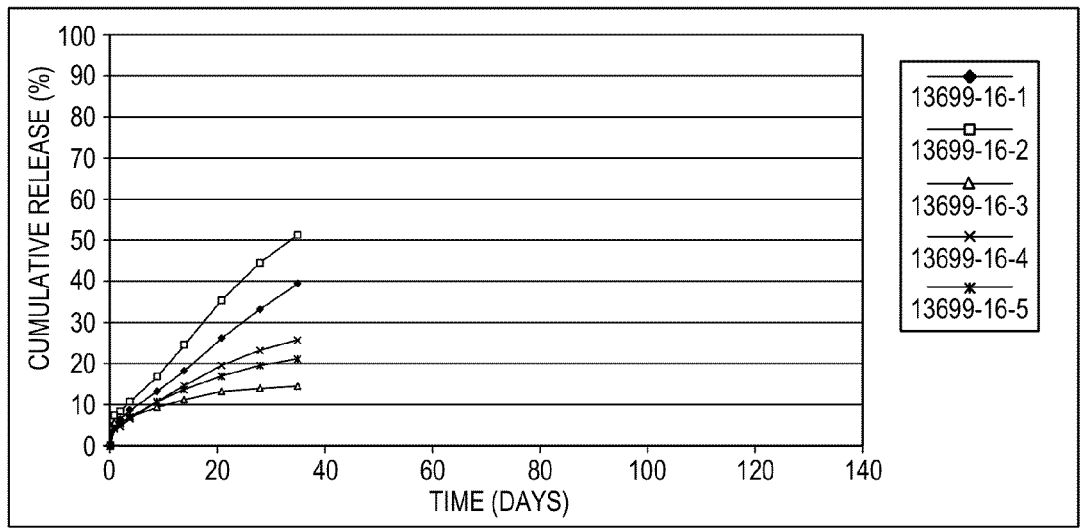
FIG. 21 is a graphic representation of the cumulative release percentage of clonidine for certain formulations.

FIG. 21 is a graphic representation of the cumulative release percentage of clonidine for certain formulations (Table 1) over about 40 days.

Figure 22:
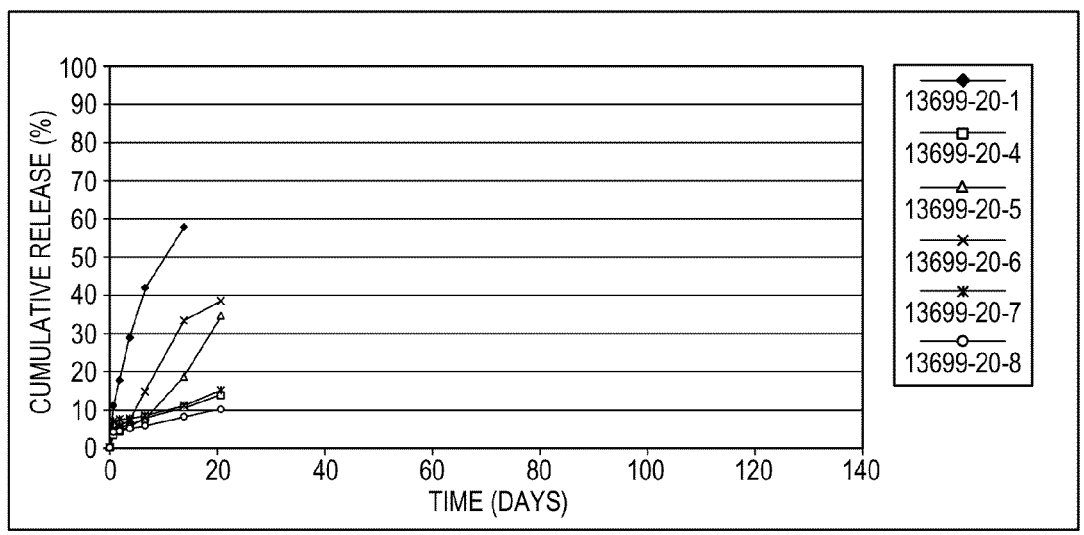
FIG. 22 is a graphic representation of the cumulative release percentage of clonidine for certain formulations.

FIG. 22 is a graphic representation of the cumulative release percentage of clonidine for certain formulations (Table 1) over about 20 days.

Figure 23:
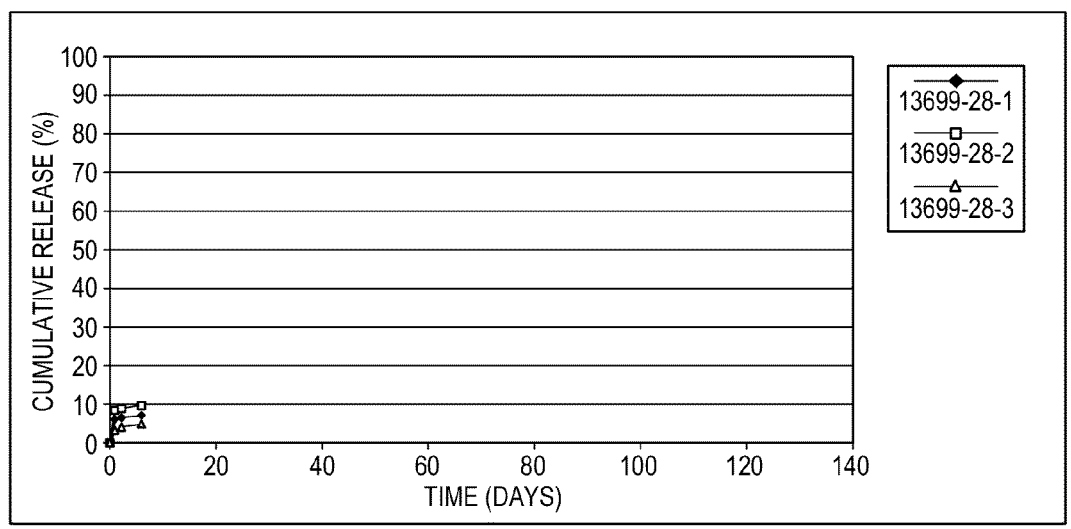
FIG. 23 is a graphic representation of the cumulative release percentage of clonidine for certain formulations.

FIG. 23 is a graphic representation of the cumulative release percentage of clonidine (Table 1) for certain formulations over 3-5 days.

Figure 24:
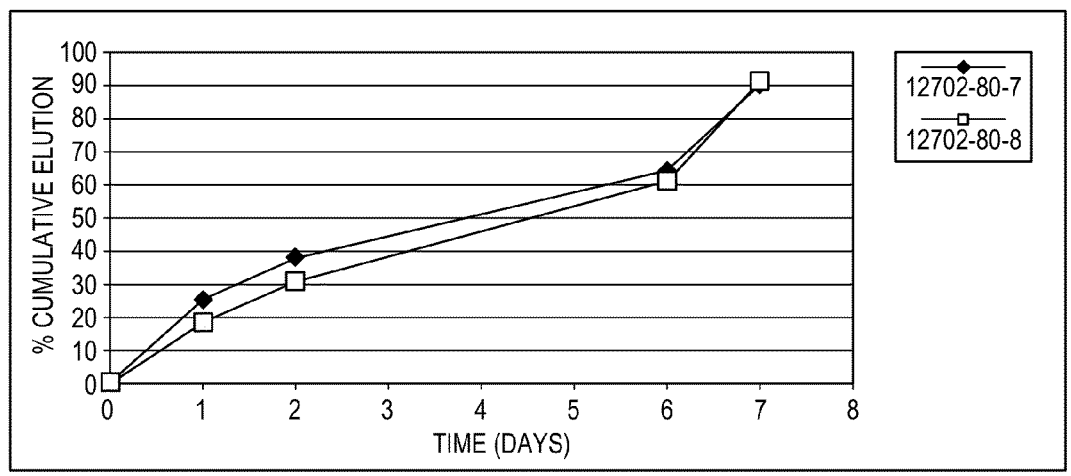
FIG. 24 is a graphic representation of the cumulative elution percentage of clonidine for certain formulations.

FIG. 24 is a graphic representation of the cumulative elution percentage of clonidine for certain formulations produced as indicated in Table 1. All formulations had about 90 cumulative release % of drug released from the depot for 7 days. The formulations here had smaller size (0.75 mm×0.75 mm), which increases surface area for release as compared to depots with larger diameters.

Figure 25:
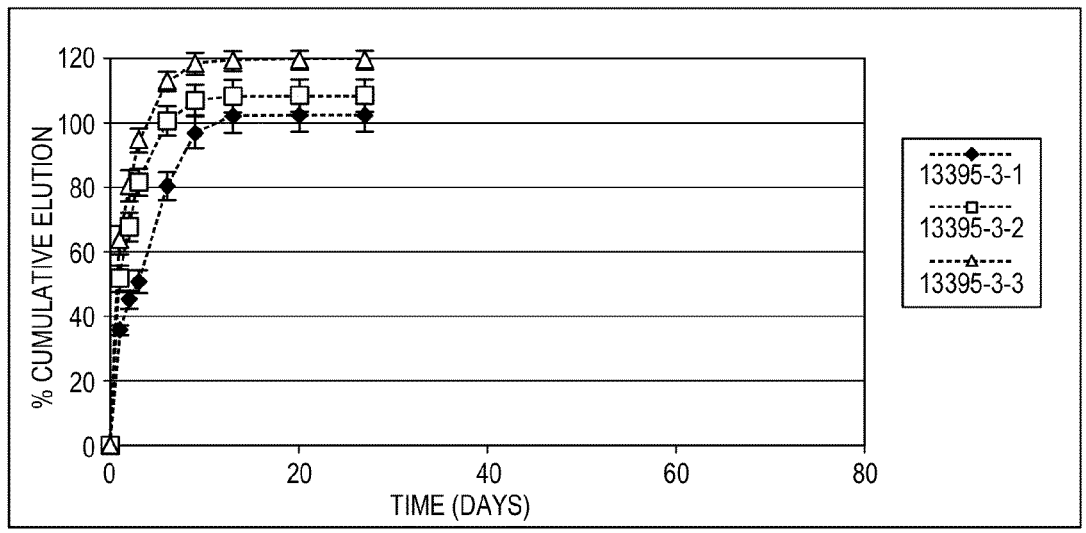
FIG. 25 is a graphic representation of the cumulative elution percentage of clonidine for certain formulations.

FIG. 25 is a graphic representation of the cumulative elution percentage of clonidine for certain formulations produced as indicated in Table 1. All formulations had over 100 cumulative release % of drug released from the depot for over 30 days.

Figure 26:
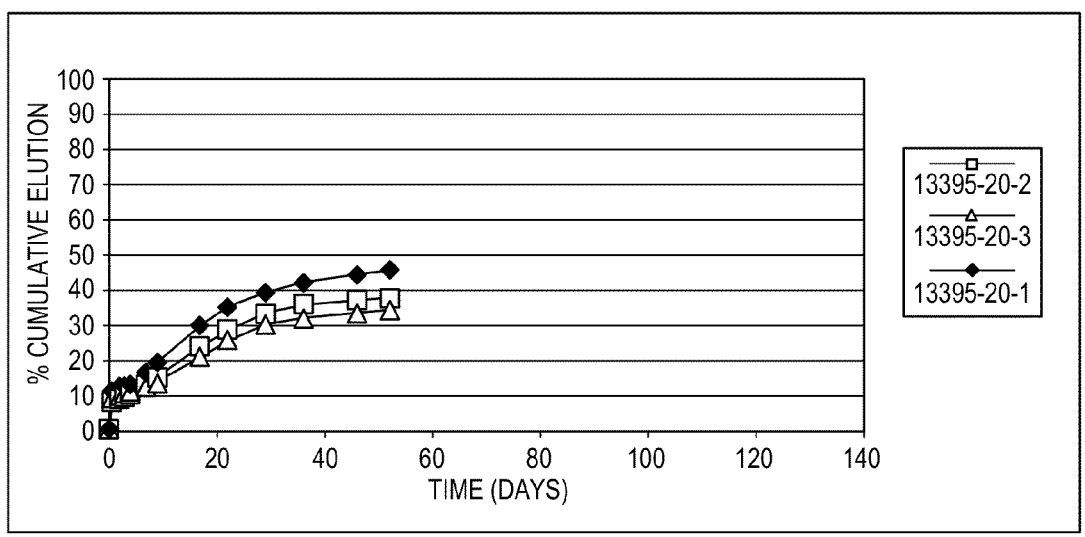
FIG. 26 is a graphic representation of the cumulative elution percentage of clonidine for certain formulations.

FIG. 26 is a graphic representation of the cumulative elution percentage of clonidine for certain formulations produced as indicated in Table 1. Span 85 is a plasticizer for one formulation. All formulations had about 30 to 50 cumulative release % of drug released from the depot for over 50 days.

Figure 27:
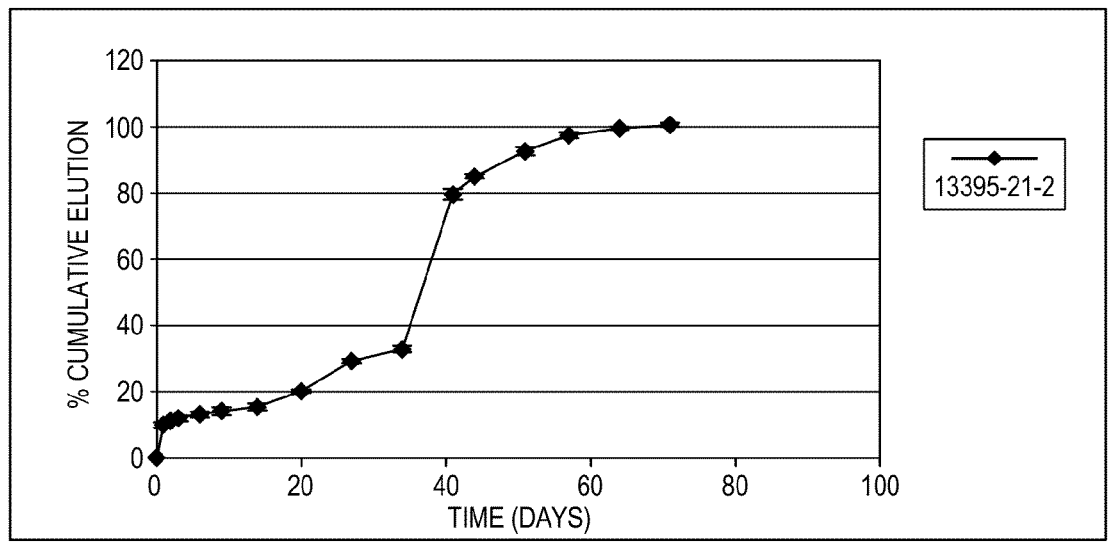
FIG. 27 is a graphic representation of the cumulative elution percentage of clonidine for one formulation.

FIG. 27 is a graphic representation of the cumulative release percentage of clonidine for one formulation produced as indicated in Table 1. The formulation containing 5 wt % clonidine drug load and the polymer 8515 PLGA had about 100 cumulative release % of drug released from the depot as long as over 75 days, which is suitable for many chronic conditions of pain and/or inflammation.

Figure 28:
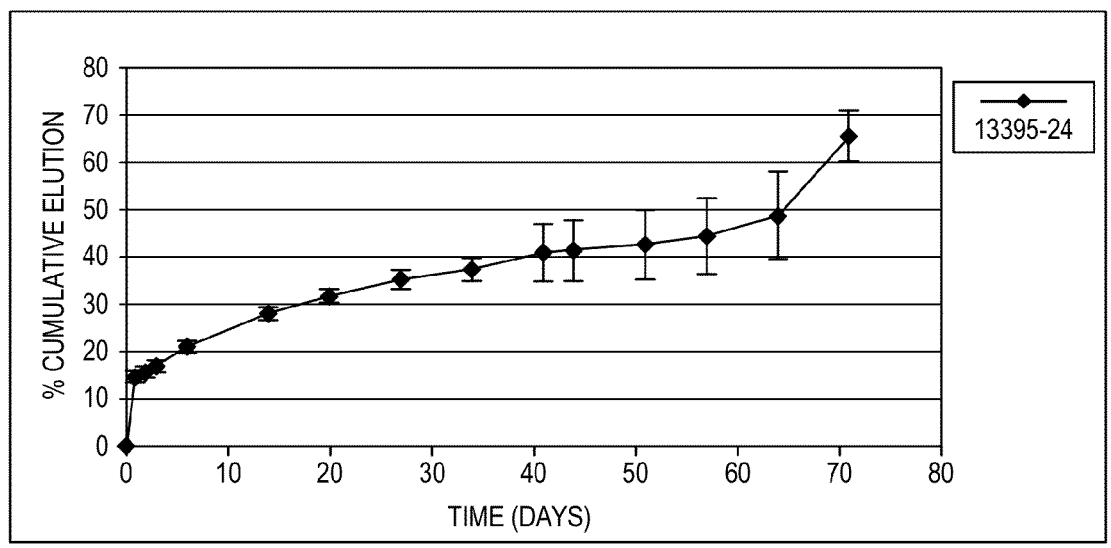
FIG. 28 is a graphic representation of the cumulative release percentage of clonidine for one formulation.

FIG. 28 is a graphic representation of the cumulative release percentage of clonidine for one formulation produced as indicated in Table 1. The formulation containing 5 wt % clonidine drug load and the polymer 8515 PLGA and Span 65 as a plasticizer had about 65 cumulative release % of drug released from the depot as long as 70 days, which is suitable for many chronic conditions of pain and/or inflammation.

Figure 29:
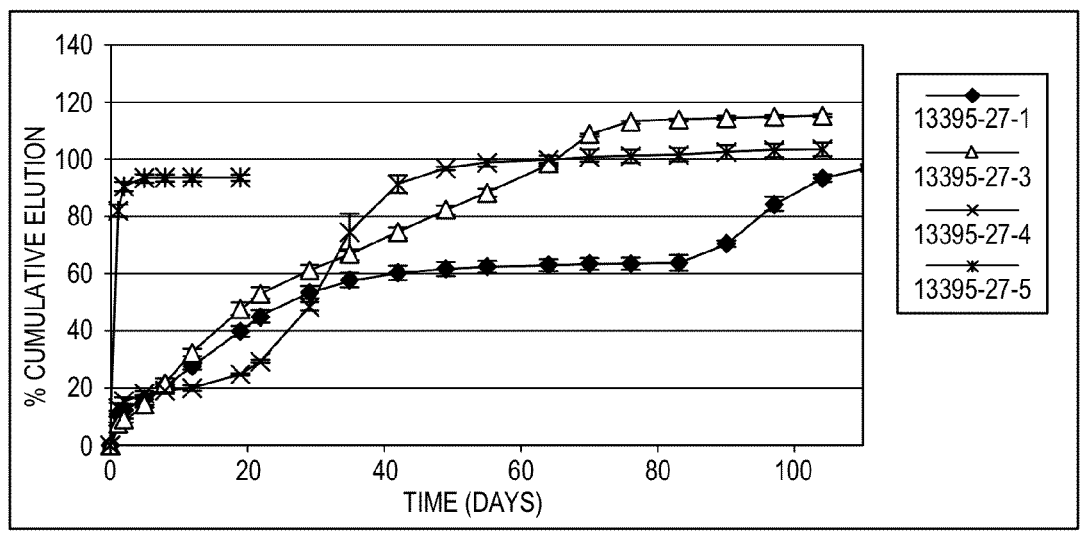
FIG. 29 is a graphic representation of the cumulative elution percentage of clonidine for certain formulations.

FIG. 29 is a graphic representation of the cumulative elution percentage of clonidine for certain formulations produced as indicated in Table 1. All formulations had about 90 to 110 cumulative release % of drug released from the depot for over 100 days, except one, which had about 90 cumulative release % of drug released from the depot for about 20 days.

Figure 30:
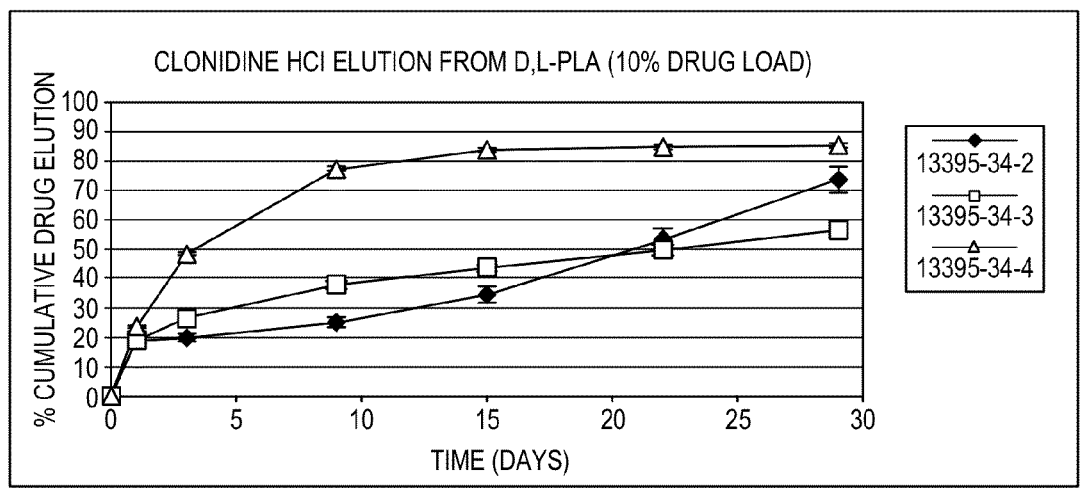
FIG. 30 is a graphic representation of the cumulative elution percentage of clonidine for certain formulations.

FIG. 30 is a graphic representation of the cumulative elution percentage of clonidine for certain formulations produced as indicated in Table 1. All formulations had about 55 to 85 cumulative release % of drug released from the depot for over 28 days.

Figure 31:
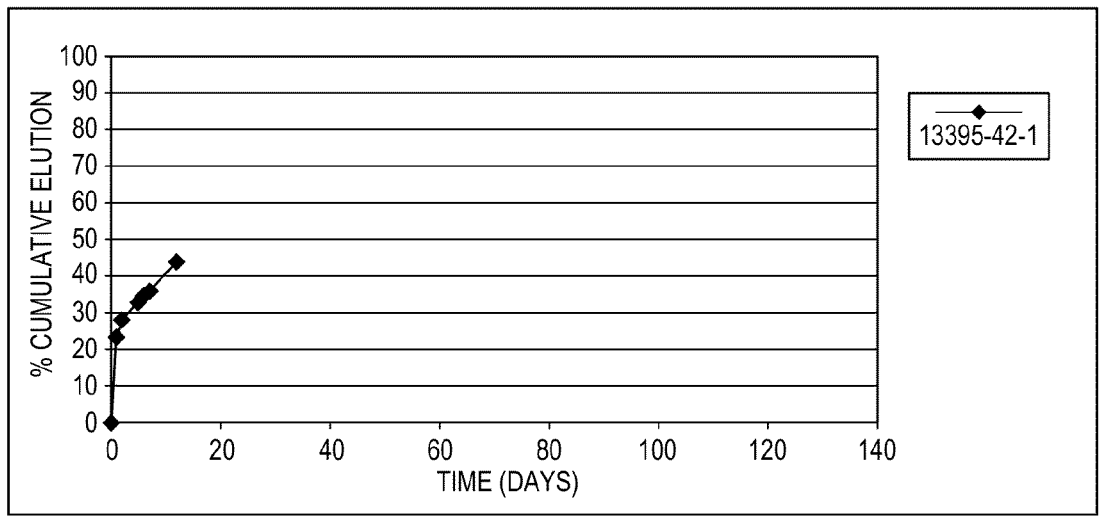
FIG. 31 is a graphic representation of the cumulative elution percentage of clonidine for one formulation.

FIG. 31 is a graphic representation of the cumulative release percentage of clonidine for one formulation produced as indicated in Table 1. The formulation containing 10 wt % clonidine drug load and the polymer DL-PLA had about 45 cumulative release % of drug released from the depot for about 18 days, which may be suitable for acute conditions of pain and/or inflammation.

Figure 32:
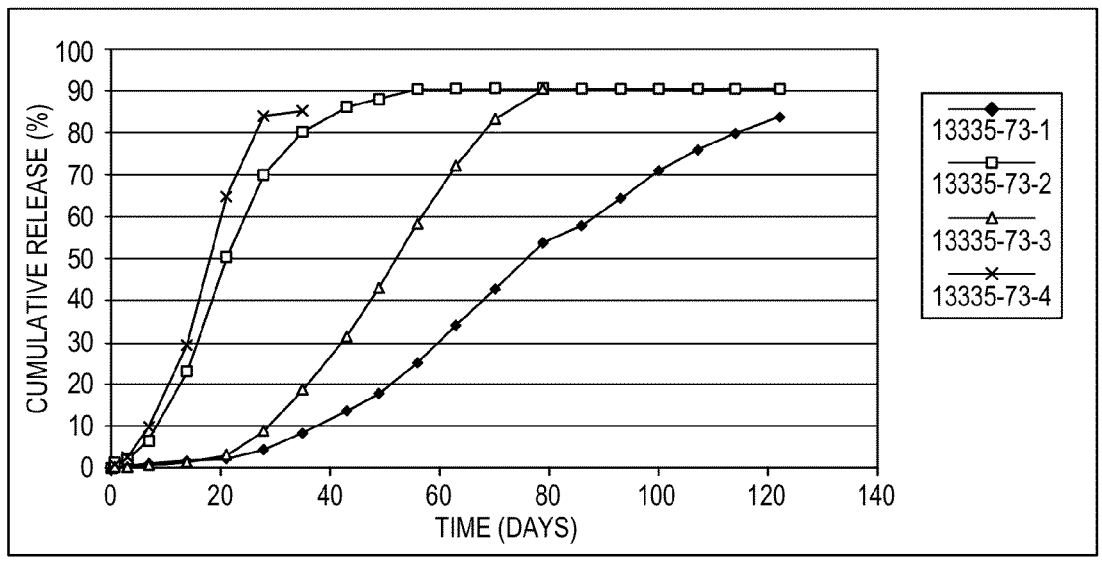
FIG. 32 is a graphic representation of the cumulative release percentage of clonidine for certain formulations.

FIG. 32 is a graphic representation of the cumulative elution percentage of clonidine for certain formulations produced as indicated in Table 2. All formulations had POE and 10% or 20% clonidine drug load. All formulations had about 80 to 90 cumulative release % of drug released from the depot for over 120 days, except one formulation, which released drug within about 35 days.

Figure 33:
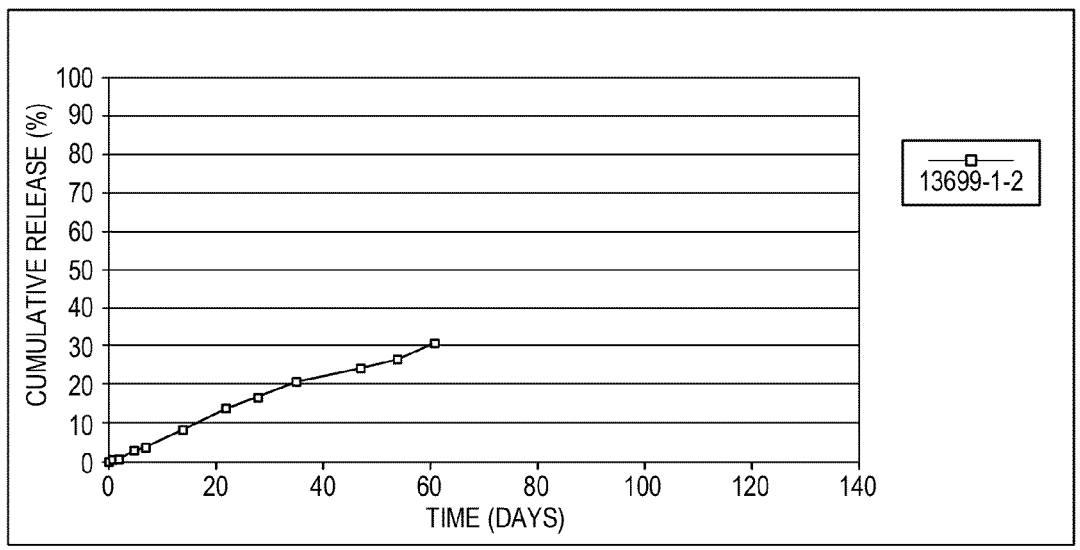
FIG. 33 is a graphic representation of the cumulative release percentage of clonidine for one formulation.

FIG. 33 is a graphic representation of the cumulative release percentage of clonidine for one formulation produced as indicated in Table 2. The formulation containing 10 wt % clonidine drug load and the polymer POE had about 60% cumulative release % of drug released from the depot for about 60 days, which may be suitable for chronic conditions of pain and/or inflammation.

Figure 34:
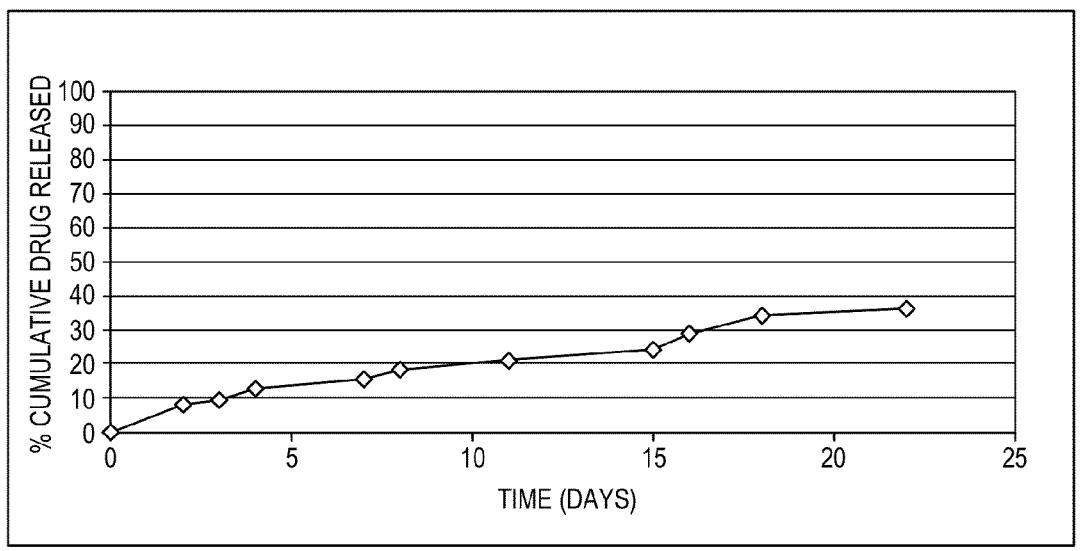
FIG. 34 is a graphic representation of the cumulative release percentage of clonidine for one formulation.

FIG. 34 is a graphic representation of the cumulative release percentage of clonidine for one formulation produced as indicated in Table 2. The formulation had about 35% cumulative release % of clonidine released from the depot for about 23 days.

The examples show different drug depot formulations useful for reducing, preventing or treating pain and/or inflammation including but not limited to inflammation and/or pain that follows surgery, acute pain and/or inflammation, chronic inflammatory diseases, chronic inflammatory bowel disease, osteoarthritis, osteolysis, tendonitis, sciatica, herniated discs, stenosis, myopathy, spondilothesis, lower back pain, facet pain, carpal tunnel syndrome, tarsal tunnel syndrome, failed back pain or the like.

Example 4

The inventors evaluated the efficacy of a various alpha-2-adrenergic receptor agonists and compared them against saline in the rat Chronic Constriction Injury model (i.e., Bennett Model) using Wistar rats. The purpose: To determine whether an alpha-2-receptor agonist can improve pain associated behavioral responses in a rat model of neuropathic pain. The doses given would mimic those achievable by a continuous release drug depot containing a biodegradable polymer (7 rats in each group).

| GRP | Drug (alpha-2-agonist) | Dose | Route |
|---|---|---|---|
| 1 | clonidine | 0.02 mg/kg | SC |
| 2 | xylazine | 8.0 mg/kg | SC |
| 3 | xylazine | 3.0 mg/kg | SC |
| 4 | romifidine | 200 mcg/kg | SC |
| 5 | romifidine | 20 mcg/kg | SC |
| 6 | dexmedetomidine | 100 mcg/kg | IP |
| 7 | dexmedetomidine | 50 mcg/kg | IP |
| 8 | saline control | 0.5 mL | SC |

Experimental Design: Four loose chromic gut ligatures, 1 mm apart, were tied around the common sciatic nerve at mid-thigh. Each group received the treatment indicated above for total of 15 days and subjected to the following two tests: (1) the Hargreaves test on days 7 and 14; and (2) the von Frey test on days 8 and 15. The results did not show any statistically significance.

Example 5

The inventors evaluated the efficacy of a various alpha-2-adrenergic receptor agonists and compared them against saline in the rat Chronic Constriction Injury model (i.e., Bennett Model) using Wistar rats. The purpose: To determine whether an alpha-2-receptor agonist can improve pain associated behavioral responses in a rat model of neuropathic pain. The doses given would mimic those achievable by a continuous release drug depot containing a biodegradable polymer (7 rats in each group).

| GRP | Drug (alpha-2-agonist) | Dose | Route |
|---|---|---|---|
| 1 | clonidine | 0.02 mg/kg | SC |
| 2 | tizanidine | 100 mcg/kg | SC |
| 3 | tizanidine | 50 mcg/kg | SC |
| 4 | medetomidine | 200 mcg/kg | SC |
| 5 | medetomidine | 100 mcg/kg | SC |
| 6 | guanfacine | 5 mg/kg | SC |
| 7 | guanfacine | 1 mg/kg | SC |
| 8 | saline control | 0.5 mL | SC |

Experimental Design: Four loose chromic gut ligatures, 1 mm apart, were tied around the common sciatic nerve at mid-thigh. Each group received the treatment indicated above for total of 15 days and subjected to the following two tests: (1) the Hargreaves test on days 7 and 14; and (2) the von Frey test on days 8 and 15.

Figure 35:
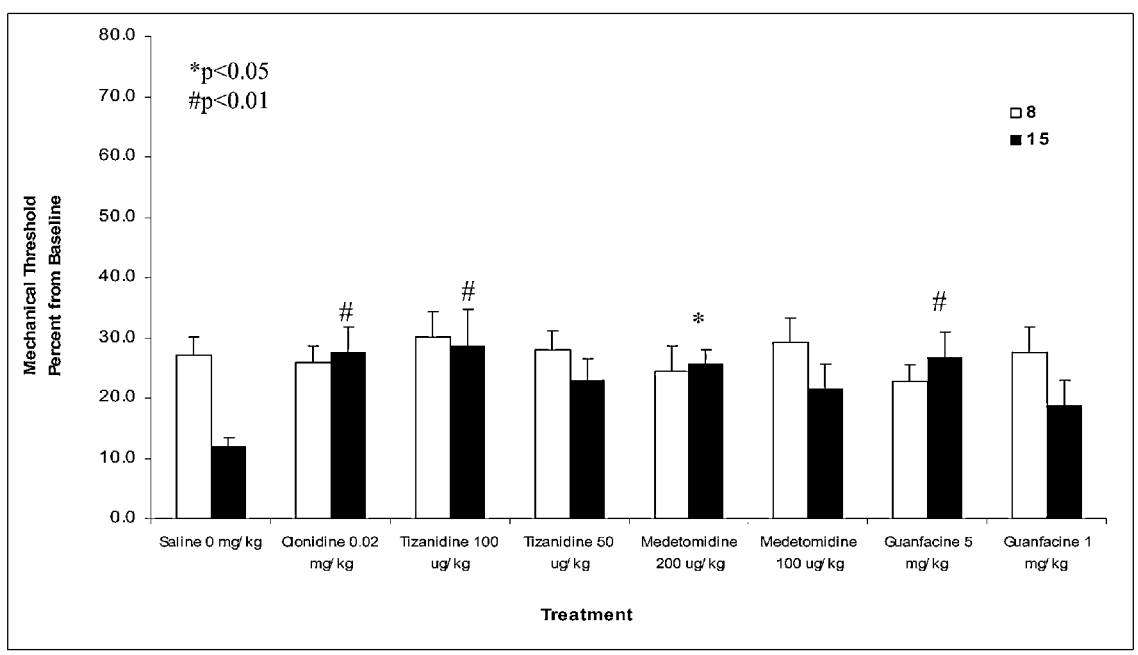
FIG. 35 is a graphic representation of the mechanical threshold as a percentage from baseline in rats given treatments of clonidine 0.02 mg/kg, tizanidine 100 micrograms/kg, tizanidine 50 micrograms/kg, medetomidine 200 micrograms/kg, medetomidine 100 micrograms/kg, guanfacine 5 mg/kg, and guanfacine 1 mg/kg subcutaneous every day for 15 days and tested for mechanical allodynia on days 8 and 15.

FIG. 35 is a graphic representation of the mechanical threshold as a percentage from baseline in rats given treatments of clonidine 0.02 mg/kg, tizanidine 100 micrograms/kg, tizanidine 50 micrograms/kg, medetomidine 200 micrograms/kg, medetomidine 100 micrograms/kg, guanfacine 5 mg/kg, and guanfacine 1 mg/kg subcutaneous every day for 15 days and tested for mechanical allodynia on days 8 and 15.

Shown in FIG. 35, the pain behavioral response (measured as a percentage of baseline) for mechanical allodynia indicates that clonidine 0.02 mg/kg, tizanidine 100 micrograms/kg, medetomidine 200 micrograms/kg, and guanfacine 5 mg/kg given subcutaneous every day for 15 days had statistically significant results of decreasing pain responses at day 15 (indicated by the # or *) when compared against saline.

Figure 36:
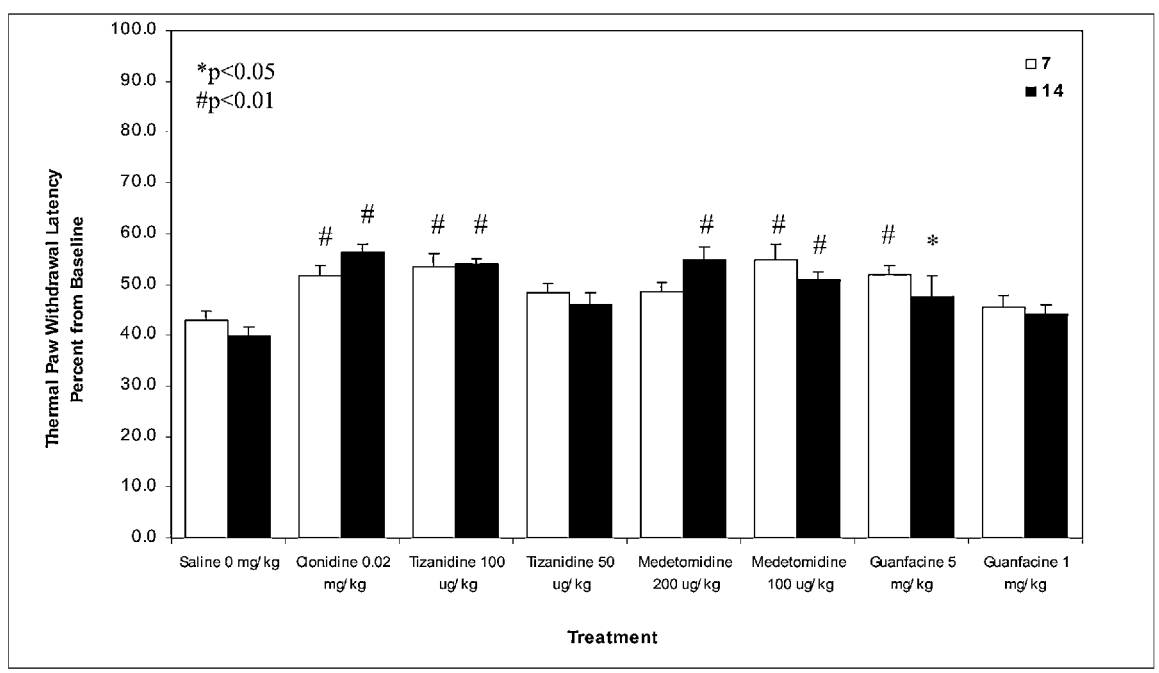
FIG. 36 is a graphic representation of the thermal paw withdrawal latency as a percentage from baseline in rats given clonidine 0.02 mg/kg, tizanidine 100 micrograms/kg, tizanidine 50 micrograms/kg, medetomidine 200 micrograms/kg, medetomidine 100 micrograms/kg, guanfacine 5 mg/kg, and guanfacine 1 mg/kg subcutaneous every day for 15 days.

FIG. 36 is a graphic representation of the thermal paw withdrawal latency as a percentage from baseline in rats given clonidine 0.02 mg/kg, tizanidine 100 micrograms/kg, tizanidine 50 micrograms/kg, medetomidine 200 micrograms/kg, medetomidine 100 micrograms/kg, guanfacine 5 mg/kg, and guanfacine 1 mg/kg subcutaneous every day for 15 days.

In FIG. 36, the pain behavioral response (measured as a percentage of baseline) for thermal hyperalgesia indicates that clonidine 0.02 mg/kg, tizanidine 100 micrograms/kg, medetomidine 100 micrograms/kg, guanfacine 5 mg/kg given subcutaneous every day for 15 days had statistically significant result of decreasing pain responses at days 7 and 14 (indicated by the # or *) and at day 14 for medetomidine 200 micrograms/kg. These results show that the alpha-2 agonists clonidine, tizanidine, medetomidine, and guanfacine may be useful in reducing, preventing, and/or treating pain and/or inflammation.

Example 6

Results from another rat chronic constriction injury model study similar to that discussed in Example 5, except some drug compositions having predominantly alpha 1 agonist activity and some drug compositions having predominantly alpha 2 agonist activity were given as indicated in the table below. The doses given would mimic those achievable by a continuous release drug depot containing a biodegradable polymer (7 rats in each group).

| GRP | Drug | Dose | Route |
|---|---|---|---|
| 1 | clonidine (alpha-2-agonist) | 0.02 mg/kg | SC |
| 2 | guanabenz (alpha-2-agonist) | 5 mg/kg | SC |
| 3 | guanabenz (alpha-2-agonist) | 1 mg/kg | SC |
| 4 | oxymetazoline (alpha-1-agonist) | 0.3 mg/kg | SC |
| 5 | oxymetazoline (alpha-1-agonist) | 0.1 mg/kg | SC |
| 6 | phenylepherine (alpha-1-agonist) | 10 mg/kg | SC |
| 7 | phenylepherine (alpha-1-agonist) | 2 mg/kg | SC |
| 8 | Saline control | 0.5 mL | SC |

Each group received the treatment indicated above for total of 14 days and the following two tests: (1) the Hargreaves test on days 7 and 14; and (2) the von Frey test on days 8 and 15.

Figure 37:
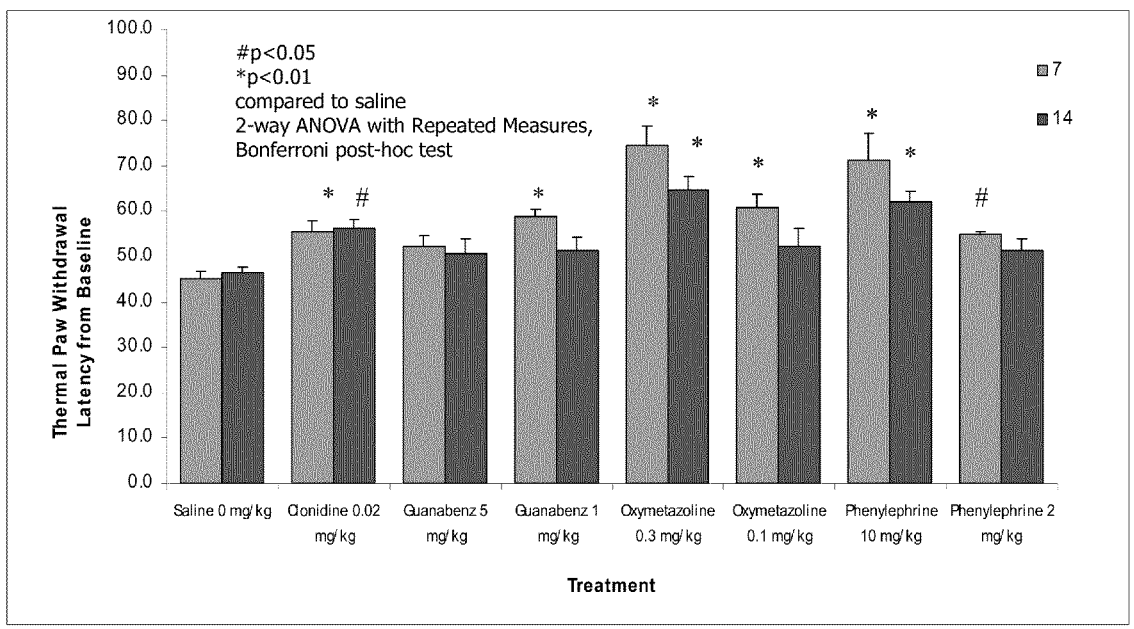
FIG. 37 is a graphic representation of the thermal paw withdrawal latency as a percentage from baseline in rats given clonidine 0.02 mg/kg, guanabenz 5 mg/kg, guanabenz 1 mg/kg, oxymetazoline 0.3 mg/kg, oxymetazoline 0.1 mg/kg, phenylephrine 10 mg/kg, and phenylephrine 2 mg/kg subcutaneous every day for 15 days.

FIG. 37 is a graphic representation of the thermal paw withdrawal latency as a percentage from baseline in rats given clonidine 0.02 mg/kg, guanabenz 5 mg/kg, guanabenz 1 mg/kg, oxymetazoline 0.3 mg/kg, oxymetazoline 0.1 mg/kg, phenylephrine 10 mg/kg, and phenylephrine 2 mg/kg subcutaneous every day for 15 days. In FIG. 37, the pain behavioral response (measured as a percentage of baseline) for thermal hyperalgesia indicates that clonidine 0.02 mg/kg, oxymetazoline 0.3 mg/kg, and phenylephrine 10 mg/kg given subcutaneous every day for 15 days had statistically significant result of decreasing pain responses at days 7 and 14 (indicated by the # or *) and at day 7 for guanabenz 1 mg/kg, oxymetazoline 0.1 mg/kg, and phenylephrine 2 mg/kg. These results show that the alpha-1 and alpha-2 agonists may be useful in reducing, preventing, and/or treating pain and/or inflammation.

Figure 38:
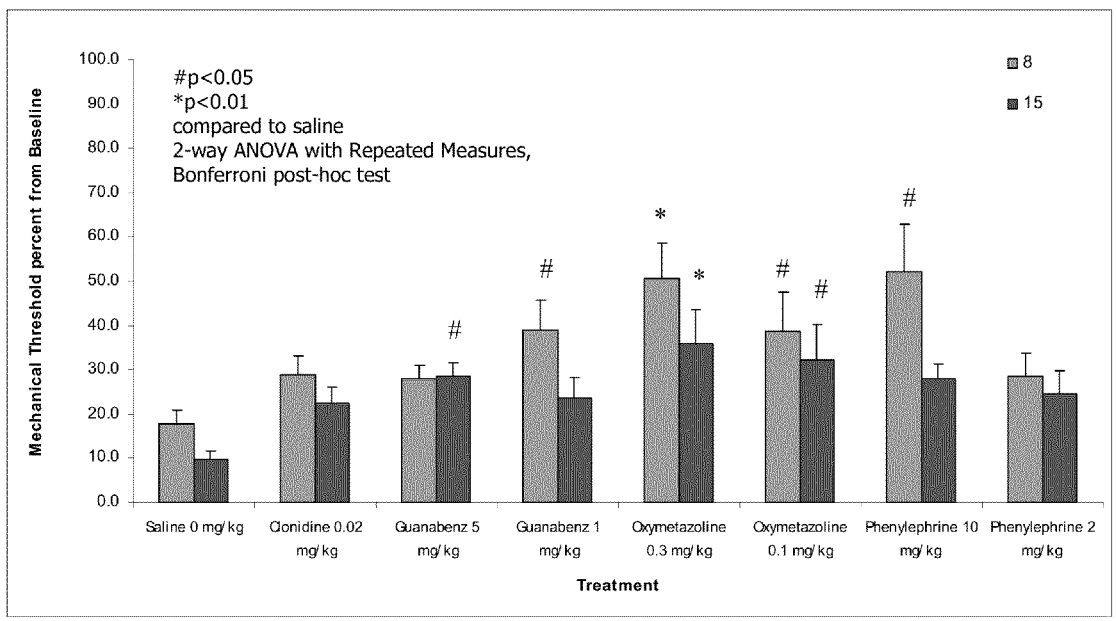
FIG. 38 is a graphic representation of the mechanical threshold as a percentage from baseline in rats given clonidine 0.02 mg/kg, guanabenz 5 mg/kg, guanabenz 1 mg/kg, oxymetazoline 0.3 mg/kg, oxymetazoline 0.1 mg/kg, phenylephrine 10 mg/kg, and phenylephrine 2 mg/kg subcutaneous every day for 15 days and mechanical allodynia tested at days 8 and 15.

FIG. 38 is a graphic representation of the mechanical threshold as a percentage from baseline in rats given clonidine 0.02 mg/kg, guanabenz 5 mg/kg, guanabenz 1 mg/kg, oxymetazoline 0.3 mg/kg, oxymetazoline 0.1 mg/kg, phenylephrine 10 mg/kg, and phenylephrine 2 mg/kg subcutaneous every day for 15 days and mechanical allodynia tested at days 8 and 15.

The pain behavioral response (measured as a percentage of baseline) for mechanical allodynia indicates that oxymetazoline 0.3 mg/kg and oxymetazoline 0.1 mg/kg subcutaneous every day for 15 days resulted in decreasing pain responses at day 8 and 15 when compared to the saline group. Guanabenz 1 mg/kg and phenylephrine 10 mg/kg decreased mechanical allodynia on day 8 when compared to saline, and Guanabenz 5 mg/kg decreased mechanical allodynia on day 15 when compared to saline. These results show that guanabenz, oxymetazoline and phenylephrine may be useful in reducing, preventing, and/or treating pain and/or inflammation.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot useful for reducing or treating pain and/or inflammation in a patient in need of such treatment, the implantable drug depot comprising a therapeutically effective amount of clonidine hydrochloride comprising about 3 wt. % to about 20 wt. % of the drug depot, the clonidine hydrochloride having a particle size of about 1 micrometer to about 250 micrometers, the drug depot being implantable at a site beneath the skin to reduce or treat pain and/or inflammation, wherein the drug depot is capable of releasing (i) a burst release of about 5% to about 20% of clonidine hydrochloride relative to a total amount of the clonidine hydrochloride loaded in the drug depot over a period of up to 72 hours, and (ii) about 21% to about 99% of clonidine hydrochloride relative to a total amount of the clonidine hydrochloride loaded in the drug depot over a subsequent period of up to 6 months, and the drug depot is solid and contains no water and comprises at least one biodegradable polymer comprising poly(D,L-lactide), poly(D,L-lactide-co-caprolactone) or poly(L-lactide-co-caprolactone) or a combination thereof and the polymer has an average molecular weight of from about 5,000 to about 500,000 and an inherent viscosity of 0.45 dL/g to 0.55 dL/g and the drug depot has a length of about 0.5 mm to about 5 mm and a diameter of about 0.01 mm to about 2 mm.

2. An implantable drug depot according to claim 1, further comprising an additional alpha-2 adrenergic agonist.

3. An implantable drug depot according to claim 2, wherein the alpha-2 adrenergic agonist further comprises L-norepinephrine, dexmetdetomidine, apraclonidine, tizanidine, brimonidine, xylometazoline, tetrahydrozoline, oxymetazoline, guanfacine, guanabenz, xylazine, moxonidine, rilmenidine, UK 14,304, B-HT 933, B-HT 920, medetomidine, mivazerol, octopamine, or a combination thereof.

4. An implantable drug depot according to claim 1, wherein the polymer comprises about 60% to 97% of the total weight % of the drug depot.

5. An implantable drug depot according to claim 2, wherein the drug depot releases 0.1 mg to 100 mg of the alpha-2 adrenergic agonist over 24 hours for a period of at least 3 days to reduce or treat pain and inflammation.

6. An implantable drug depot according to claim 1, wherein the drug depot comprises from about 5 wt. % to about 15 wt. % of clonidine hydrochloride, and at least 80 wt. % of a biodegradable polymer based on the total weight of the drug depot.

7. An implantable drug depot according to claim 1, wherein the drug depot is in the form of a pellet.

8. An implantable drug depot according to claim 1, wherein the alpha-2 adrenergic agonist has a particle size of about 5 micrometers to about 30 micrometers.

9. An implantable drug depot according to claim 1, wherein the polymer has an average molecular weight of about 20,000 to about 50,000.

10. An implantable drug depot according to claim 1, wherein the polymer has an average molecular weight of about 10,000 to about 100,000.

11. An implantable drug depot according to claim 1, wherein the drug depot has a modulus of elasticity of $2 \times 10^4$ to about $5 \times 10^5$ dynes/cm$^2$.

12. An implantable drug depot according to claim 1, wherein the drug depot has a length of 5 mm.

13. An implantable drug depot according to claim 1, wherein the drug depot is configured for use in humans.

14. An implantable drag depot useful for reducing or treating pain and/or inflammation in a patient in need of such treatment, the implantable drug depot comprising a therapeutically effective amount of clonidine hydrochloride comprising about 5 wt. % to about 8 wt. % of the drug depot, the clonidine hydrochloride having a particle size of about 1 micrometer to about 250 micrometers, the drug depot being implantable at a site beneath the skin to reduce or treat pain and/or inflammation, wherein the drug depot is capable of releasing (i) a burst release of not more than 7% of the clonidine hydrochloride relative to a total amount of the clonidine hydrochloride loaded in the drug depot within the first five days, and (ii) about 21% to about 99% of clonidine hydrochloride relative to a total amount of the clonidine hydrochloride loaded in the drug depot over a subsequent period of up to 6 months, and the drug depot comprises at least one biodegradable polymer comprising poly(D,L-lactide), poly(D,L-lactide-co-caprolactone) or poly(L-lactide-co-caprolactone) or a combination thereof and the polymer has an average molecular weight of from about 5,000 to about 500,000 and an inherent viscosity of 0.45 dL/g to 0.55 dL/g and the drug depot has a length of about 0.5 mm to about 5 mm and a diameter of about 0.01 mm to about 2 mm.

* * * * *

UNITED STATES PATENT AND TRADEMARK OFFICE
CERTIFICATE OF CORRECTION

PATENT NO. : 8,889,173 B2
APPLICATION NO. : 12/424271
DATED : November 18, 2014
INVENTOR(S) : Zanella et al.

Page 1 of 1

It is certified that error appears in the above-identified patent and that said Letters Patent is hereby corrected as shown below:

In the Claims

In Column 54, Line 14, in Claim 14, delete "drag" and insert -- drug --, therefor.

Signed and Sealed this
Twenty-fifth Day of August, 2015

Michelle K. Lee
*Director of the United States Patent and Trademark Office*